United States Patent
Mizuno et al.

(10) Patent No.: US 10,066,199 B2
(45) Date of Patent: Sep. 4, 2018

(54) FOREIGN SUBSTANCE INTRODUCTION DEVICE AND METHOD OF PRODUCING CELLS WITH INTRODUCED FOREIGN SUBSTANCE

(71) Applicant: NATIONAL UNIVERSITY CORPORATION TOYOHASHI UNIVERSITY OF TECHNOLOGY, Toyohashi-shi (JP)

(72) Inventors: Akira Mizuno, Nagoya (JP); Rika Numano, Toyohashi (JP); Hirofumi Kurita, Toyohasi (JP)

(73) Assignee: NATIONAL UNIVERSITY CORPORATION TOYOHASHI UNIVERSITY OF TECHNOLOGY (JP)

( * ) Notice: Subject to any disclaimer, the term of this patent is extended or adjusted under 35 U.S.C. 154(b) by 339 days.

(21) Appl. No.: 14/650,560

(22) PCT Filed: Dec. 12, 2013

(86) PCT No.: PCT/JP2013/083374
§ 371 (c)(1),
(2) Date: Aug. 19, 2015

(87) PCT Pub. No.: WO2014/092164
PCT Pub. Date: Jun. 19, 2014

(65) Prior Publication Data
US 2015/0368604 A1    Dec. 24, 2015

(30) Foreign Application Priority Data
Dec. 12, 2012 (JP) .................. 2012-271810

(51) Int. Cl.
C12M 1/42 (2006.01)
C12N 15/87 (2006.01)
C12N 13/00 (2006.01)

(52) U.S. Cl.
CPC .............. *C12M 35/02* (2013.01); *C12N 13/00* (2013.01); *C12N 15/87* (2013.01)

(58) Field of Classification Search
CPC ....................................... C12M 35/02
(Continued)

(56) References Cited

U.S. PATENT DOCUMENTS 6,482,306 B1 * 11/2002 Yager .................. B01F 13/0001
137/808
2006/0115888 A1    6/2006 Gamelin et al.
(Continued)

FOREIGN PATENT DOCUMENTS

EP        1578966 A1    9/2005
JP    2006-508663 A    9/2006
(Continued)

OTHER PUBLICATIONS

Lee et al., "Electrophoretic motion of a charged water droplet near an oil-air interface," May 20, 2012, Applied Physics Letters, 100, 221602 (Year: 2012).*
(Continued)

*Primary Examiner* — Kevin Joyner
*Assistant Examiner* — Holly Michaela Mull
(74) *Attorney, Agent, or Firm* — Day Pitney LLP

(57) ABSTRACT

An exogenous substance transfer apparatus that introduces an exogenous substance into a small amount of cells by electrical action and a method for manufacturing exogenous substance-bearing cells at low cost are provided.
In the introducing an exogenous substance like a gene into a cell, a cell suspension liquid that contains the cell and the (Continued)

exogenous substance is supplied to a container through an opening portion in an amount that is prepared such that a liquid droplet that is formed will not come into contact with a pair of electrodes simultaneously. The liquid droplet is formed in an oil stored in the container, without the cell suspension liquid mixing with the oil. When a direct current voltage is supplied to the electrodes from a power supply, the liquid droplet moves there-between, and the exogenous substance is introduced into the cell within the liquid droplet by electrical action.

14 Claims, 41 Drawing Sheets

(58) Field of Classification Search
USPC ...................................................... 435/285.2
See application file for complete search history.

(56) References Cited

U.S. PATENT DOCUMENTS

| | | | |
|---|---|---|---|
| 2007/0275454 | A1 | 11/2007 | Chang et al. |
| 2008/0138876 | A1 | 6/2008 | Ragsdale |
| 2011/0263005 | A1 | 10/2011 | Chang et al. |
| 2012/0058467 | A1* | 3/2012 | Thomas ............... B01L 3/5085 435/6.1 |
| 2013/0122592 | A1 | 5/2013 | Hayakawa et al. |
| 2015/0093813 | A1 | 4/2015 | Chang et al. |

FOREIGN PATENT DOCUMENTS

| | | | |
|---|---|---|---|
| JP | 2010-178746 | A | 8/2010 |
| JP | 2011-516096 | A | 5/2011 |
| JP | 2011-147399 | A | 8/2011 |
| WO | 2004050866 | A1 | 6/2004 |
| WO | 2014092164 | A1 | 6/2014 |

OTHER PUBLICATIONS

A. Asada, H. Aoki, H. Kurita, A. Antoniu, H. Yasuda, K. Takashima, and A. Mizuno, "A novel gene transformation technique using water-in-oil droplet in an electrostatic field", IEEE Transactions on Industry Applications, Jan. 2013, vol. 49, p. 311-315.

Translation of Written Opinion of the International Searching Authority in corresponding PCT Application No. PCT/JP2013/083374, dated Mar. 18, 2014, 3 pages.

Asada, Atsushi et al., "Denkaichu no Yuchu Ekiteki o Mochiiru Idenshi Donyuho no Kaihats," 2011, Proceedings of Annual Meeting of the Institute of Alectrostatics Japan 2011, pp. 155-159.

International Preliminary Report on Patentability issued in corresponding international application No. PCT/JP2013/083374, dated Mar. 18, 2014. (in the English and Japanese languages).

Yolanda Schaerli et al, "The potential of microfluidic water-in-oil droplets in experimental biology", Molecular Biosystems, GB, (Oct. 12, 2009), vol. 5, No. 12, ISSN 1742-206X, p. 1392-1404, XP055270349 [A] 1-15 p. 1393 col. 2 par.1, p. 1399 col. 2 par.4.

Supplementary European Search Report in related European application No. EP 13 86 1819, dated May 13, 2016.

A. Asada, et al., "A novel gene transformation technique using water-in-oil droplet in an electrostatic field", the 35th Annual Meeting of the of the Institute of Electrostatics Japan, Tokyo University of Science, Sep. 11, 2011, p. 155-158.

English Translation of International Search Report and Written Opinion of the International Searching Authority in corresponding PCT Application No. PCT/JP2013/083374, dated Mar. 18, 2014, 3 pages.

Asada, Atsushi et al., "Denkaichu no Yuchu Ekiteki o Mochiiru Idenshi Donyuho no Kaihats," 2011, Proceedings of Annual Meeting of the Institute of Alectrostatics Japan 2011, pp. 155-159. (with English translation).

Japanese Office Action issued in corresponding application No. JP 2014-552090, dated Aug. 29, 2017.

* cited by examiner

FOREIGN SUBSTANCE INTRODUCTION DEVICE AND METHOD OF PRODUCING CELLS WITH INTRODUCED FOREIGN SUBSTANCE

RELATED APPLICATIONS

This application claims priority to PCT Application No. PCT/JP2013/083374, filed Dec. 12, 2013, which itself claims priority to Japanese Application No. 2012-271810, filed Dec. 12, 2012, the disclosure and teachings of which are incorporated herein by reference.

TECHNICAL FIELD

The present invention relates to an exogenous substance transfer apparatus that introduces an exogenous substance such as an exogenous gene or the like into a cell and to a method for manufacturing exogenous substance-bearing cells into which an exogenous substance has been introduced.

BACKGROUND ART

Various types of methods have been developed for introducing an exogenous substance, such as DNA, RNA, a protein, a chemical agent, or the like, into a target cell. Techniques for introducing an exogenous substance into a target cell are broadly divided into biological techniques, chemical techniques, and physical techniques. One known biological technique is a method that uses a virus. Generally known chemical techniques include the calcium phosphate method and the lipofection method. Physical techniques include the electroporation method, the gene gun (particle gun) method, methods that use ultrasound, and the like. It is known that in bacteria such as *Escherichia coli* and the like, DNA is easily introduced into a cell by applying heat shock to a cell that has been made artificially competent in the presence of calcium chloride. The method of applying heat shock is widely used for the genetic transformation of the *E. coli*.

The biological method that uses a virus requires special research facilities for the containment of viral infection. Moreover, the biological method that uses a virus poses the problem that the cell into which the virus is introduced may become cancerous due to the toxicity, antigenicity, and the like of the virus. The calcium phosphate method does not require a special apparatus. The reagents that are necessary in order to apply the calcium phosphate method are inexpensive. However, with the calcium phosphate method, damage to the target cell is comparatively great, and the transfection efficiency is poor. The lipofection method has a better transfection efficiency than does the calcium phosphate method, and it has the advantage of requiring only a small amount of DNA (the exogenous substance). However, with the lipofection method, the number of parameters to be examined is comparatively great, depending on the target cell, and an expensive reagent is required. With the chemical techniques, the toxicity of the reagent limits the types of cells that can be used, and in a case where a cell type such as a hippocampal neuron or the like is used as the target cell, a good transfection efficiency is difficult to achieve.

In comparison to the biological techniques and the chemical techniques that are described above, the advantages of the physical techniques are that toxicity to the cell does not need to be considered and an expensive reagent is not required. With the gene gun method, gold particles that have been coated with an exogenous gene (for example, DNA) are shot into the target cell by high-pressure helium gas, such that the exogenous gene is introduced directly into the nucleus of the target cell. In this manner, the gene gun method is able to introduce an exogenous gene into the target cell and cause the gene to be expressed. That is, the gene gun method is a method that shoots a large number of DNA molecules into the target cell. Therefore, with the gene gun method, the amount of gene expression in a single cell is great, but the expression efficiency is poor in the sense that a large number of cells must be defined as the target cells in order to introduce the gene into a significant number of cells. The methods that use ultrasound are not simple, because they require that conditions be set separately for each type of cell by trial and error.

The electroporation method is the most representative of the physical techniques, and it is a method that causes DNA and the like to be incorporated into the cell by the application of a high-voltage pulse to the cell, such that pores are temporarily created in the cell membrane through which exogenous substances can pass. The electroporation method achieves a higher transfection efficiency than do the chemical techniques, it is easy to perform and is highly safe and reproducible, and it can be applied to various types of organisms (including plant cells) and various types of cells.

The electroporation method is a method in which processing is performed in a state in which electrodes are immersed in a liquid suspension that contains cells and an exogenous substance. Therefore, with the electroporation method, when the processing is performed several times using the same electrodes, there is a strong possibility that a new liquid suspension will be contaminated by the old suspension that has adhered to the electrodes. Contamination can be avoided by discarding the used electrodes after each round of processing, but that increases the cost of the processing.

Furthermore, with the electroporation method, a comparatively large sample volume is required, making it necessary to prepare a large amount of scarce cells. Therefore, with the electroporation method, the possibility exists that analysis will be difficult in a case where the amount of cells within the sample is small. Methods that have been proposed for reducing the amount of the sample that is required include a method for performing electroporation by filling a hollow capillary tube or a tube with a sample (Patent Literature 1), a method for improving the transfection efficiency of the exogenous gene (Patent Literature 2), and a pipette tip type electroporation apparatus (Patent Literature 3). However, in clinical practice, such as in gene therapy, cell transplantation, and the like, it is best to harvest as few cells as possible in order to reduce the burden on the patient, and demand has also grown for further reductions in the amount of high-cost exogenous genes that are used.

In addition, with the electroporation method, an expensive pulse generator is required, and in many cases, studies of the optimum conditions for introducing exogenous substances become complicated.

The inventors have developed an apparatus that is provided with a container that is filled with oil, two electrodes that are affixed in parallel to a bottom face of the container, and a high-voltage direct current power supply, with one of the electrodes serving as a high-voltage electrode and the other electrode serving as a ground electrode, and the apparatus applying voltage from the high-voltage direct current power supply. The inventors discovered that, by placing a hydrophilic liquid droplet that contains plasmid DNA and competent cells of *E. coli* between the electrodes and applying a voltage, while moving the liquid droplet back and forth between the electrodes, the plasmid DNA (an exogenous substance) can be introduced into the *E. coli* in the drop of liquid using a sample with a volume of only two microliters. The inventors proposed a new electroporation technology that is able to make an expensive pulse generator unnecessary (Non-Patent Literature 1, 2).

CITATION LIST

Patent Literature

Patent Literature 1: Japanese Laid-Open Patent Publication No. 2010-178746
Patent Literature 2: Japanese Laid-Open Patent Publication No. 2011-147399
Patent Literature 3: Japanese Unexamined Patent Application Publication No. 2011-516096

Non-Patent Literature

Non-Patent Literature 1: A. Asada, et al., "A novel gene transformation technique using water-in-oil droplet in an electrostatic field", the 35th Annual Meeting of the of the Institute of Electrostatics Japan, Tokyo University of Science, Sep. 13, 2011, p. 155-158.
Non-Patent Literature 2: A. Asada, H. Aoki, H. Kurita, A. Antoniu, H. Yasuda, K. Takashima, and A. Mizuno, "A novel gene transformation technique using water-in-oil droplet in an electrostatic field", IEEE Transactions on Industry Applications, January 2013, vol. 49, p. 311-315.

SUMMARY OF INVENTION

In the method that is described above, the liquid droplet moves back and forth between the electrodes while skipping along upwardly projecting lines of electric force. Therefore, one problem with the method that is described above is that the movement of the liquid droplet is unstable, which causes variability in the transfection efficiency. Another problem with the method that is described above is that the processing may be interrupted due to the inability of the liquid droplet to separate from the electrodes.

In addition, test results for the method that is described above are from tests that used *E. coli*, into which genes can be introduced easily by heat shock, and it is not known whether the method can be applied to other cells, such as animal cells and the like, for which the barriers to introduction are greater.

In the method that is described above, measures to avoid contamination have not been taken into account, and problems remain. Therefore, in the field of technologies for introducing an exogenous substance into a target cell, technologies that can sufficiently reduce the minimum required amount of cells and the minimum required amount of the exogenous substance with respect to a wide variety of cell types, and that can also perform the processing at low cost, have not yet been provided. It is therefore difficult to produce cells into which an exogenous substance has been introduced (exogenous substance-bearing cells) at low cost.

It is an object of the present invention to provide an apparatus that uses an electrical effect to introduce an exogenous substance into a small amount of cells efficiently and at low cost, and to provide a method for manufacturing exogenous substance-bearing cells that is able to manufacture various types of exogenous substance-bearing cells at low cost.

According to a first aspect of the present invention, an exogenous substance transfer apparatus that introduces an exogenous substance into a cell from outside the cell by electrical action is provided. The exogenous substance transfer apparatus includes at least one storage vessel, at least one electrode portion, and an electric field generating portion. The at least one storage vessel has an opening through which a substance can be supplied from the outside. Each of the at least one electrode portion includes a pair of electrodes. The at least one electrode portion is disposed inside each of the at least one storage vessel. The pair of electrodes is separated from one another and extends in a direction that is intersectional to a horizontal plane. The electric field generating portion is configured to generate an electric field by applying a direct current voltage to the at least one electrode portion for a specified length of time. The electric field generating portion is configured, when applying the direct current voltage to the at least one electrode portion, to cause a liquid droplet of a cell suspension liquid to move toward an opposite polarity electrode and to cause the liquid droplet to reverse its direction of movement by causing the liquid droplet to come into contact with the opposite polarity electrode. The opposite polarity electrode is one of the pair of the electrodes whose polarity is an opposite of a polarity of the liquid droplet. The direct current voltage is applied in a state in which the cell suspension liquid has been supplied between the pair of the electrodes in each of the at least one storage vessel storing an insulating liquid to form the liquid droplet in the insulating liquid. The cell suspension liquid contains an exogenous substance and a cell. The cell suspension liquid is not capable of being mixed with the insulating liquid, the liquid droplet having a diameter smaller than a gap between the pair of the electrodes.

To say that the electric field causes the liquid droplet to move means that the direction of movement of the liquid droplet in the horizontal plane is at least one of a direction from a positive electrode to a negative electrode and a direction from a negative electrode to a positive electrode along lines of electric force that describe the electric field. It does not mean that the liquid droplet moves strictly along the virtual lines of electric force both in a horizontal direction and in a vertical direction that is orthogonal to the horizontal direction.

According to the exogenous substance transfer apparatus in the first aspect, the insulating liquid is stored in the storage vessel, and when the cell suspension liquid, which contains the exogenous substance and the cell and is not capable of being mixed with the insulating liquid, is supplied through the opening, the independent liquid droplet is formed within the insulating liquid. When the direct current voltage is applied by the electric field generating portion to the pair of the electrodes inside the storage vessel for the specified length of time, the electric field is generated between the pair of the electrodes. An electrical charge is induced on the surface of the liquid droplet by the applying of the voltage, and the liquid droplet is moved by Coulomb's force toward the opposite polarity electrode along the virtual lines of electric force that describe the electric field that is formed between the pair of the electrodes. The liquid droplet comes into contact with the opposite polarity electrode that is disposed in the direction of liquid droplet's movement. Because the outside diameter of the liquid droplet is smaller than the gap between the pair of the electrodes, the liquid droplet does not come into contact with both of the electrodes at the same time. When the liquid droplet comes into contact with the opposite polarity electrode, that triggers the reversal of the liquid droplet's direction of movement, and the liquid droplet starts to move toward the opposite side. It is presumed that the electrical action on the liquid droplet that is generated by the contact with the electrode makes it possible for the exogenous substance to be introduced into the cell inside the liquid droplet.

In the exogenous substance transfer apparatus in the first aspect, an expensive pulse generator is not required. Accordingly, the exogenous substance transfer apparatus in the first aspect is able to make the apparatus simpler than in the known electroporation method and can provide the apparatus for introducing the exogenous substance into the cell at a low cost. Because the pair of the electrodes extend in a direction that is intersectional to the horizontal plane, the lines of electric force that describe the electric field that is generated by the applying of the voltage to the pair of the electrodes include lines of electric force that extend in the horizontal direction. In a case where the liquid droplet is moved up and down by the action of the electric field, the movement of the liquid droplet tends to become unstable. In the present apparatus, the liquid droplet is moved in the horizontal direction by the action of the electric field and moves in a stable manner, so the present apparatus can prevent the liquid droplet from ceasing to move because the liquid droplet is kept in contact with the electrode by the force of gravity. Therefore, the operation of introducing the exogenous substance can be performed smoothly and efficiently in the present apparatus.

According to the present apparatus, the exogenous substance can be introduced into various types of cells with a good transfection efficiency, and a good survival rate can be achieved in the cells after the exogenous substance is introduced. The amount of the cell suspension liquid that is necessary in order to perform the processing needs only to be an amount that forms a minute liquid droplet. Therefore, in a case where a genetic transformation is carried out by introducing an exogenous gene (DNA) into a cell, for example, the present apparatus is able to reduce the amount that is used of the cell suspension liquid that contains the exogenous gene and the cell to far below what is used by the known techniques, making it possible to dramatically reduce the number of cells and the amount of the exogenous gene that are required.

In the exogenous substance transfer apparatus in the first aspect, the pair of the electrodes may be formed into shapes that, in a case where a plurality of virtual lines of electric force are drawn on a surface of the insulating liquid when the direct current voltage is applied to each of the at least one electrode portion, cause the plurality of the lines of electric force to be distributed such that they are locally concentrated.

According to the exogenous substance transfer apparatus in this case, it is possible to move the liquid droplet smoothly even if the voltage that is applied by the electric field generating portion is reduced.

The present apparatus moves the liquid droplet in the insulating liquid by the force of electrical attraction, so if the voltage that is applied to the electrode portion is too small, it becomes difficult to move the liquid droplet. On the other hand, if the voltage that is applied to the electrode portion is too great, the liquid droplet will burst, or a short circuit will be created because the liquid droplet becomes elongated and connects both electrodes. If the pair of the electrodes are formed into shapes that cause the lines of electric force to be distributed such that they are locally concentrated, the electrical action can be locally strengthened even if the voltage that is applied to the pair of the electrodes is small. Therefore, the present apparatus is able to move the liquid droplet smoothly, even as it avoids a short circuit and the bursting of the liquid droplet by reducing the applied voltage. The present apparatus is therefore able to improve the reproducibility and the reliability of the processing that introduces the exogenous sub stance.

In the exogenous substance transfer apparatus in the first aspect, one of the pair of the electrodes may include a first sheet portion. The first sheet portion is a sheet portion that extends in a direction that is substantially orthogonal to the horizontal plane. The first sheet portion is a sheet portion that is formed to be curved into a substantially circular arc in which a side that faces the other electrode is dented.

According to the exogenous substance transfer apparatus in this case, it is possible to move the liquid droplet in a more stable manner because one of the electrodes includes the first sheet portion. Moreover, in the present apparatus, the first sheet portion can be easily formed by bending a single metal plate or metal foil, for example. The present apparatus is therefore able to lower the manufacturing cost of the apparatus.

In the exogenous substance transfer apparatus in the first aspect, another of the pair of the electrodes may include a second sheet portion. The second sheet portion is a sheet portion that extends in a direction that is substantially orthogonal to the horizontal plane. The second sheet portion is a sheet portion that is formed to be curved into a substantially circular arc in which a side that faces the one of the electrodes is dented.

According to the exogenous substance transfer apparatus in this case, one electrode of the pair of the electrodes includes the first sheet portion, and the other electrode includes the second sheet portion. Accordingly, the present apparatus is able to move the liquid droplet in a more stable manner than in a case where the other electrode does not include the second sheet portion. Moreover, if the shapes of the pair of the electrodes are the same, the present apparatus can reduce the processing cost for the pair of the electrodes, because the parts can be common.

In the exogenous substance transfer apparatus in the first aspect, at least one of the pair of the electrodes may include one of concave portion and convex portion.

According to the exogenous substance transfer apparatus in this case, one of a recessed portion and a raised portion is formed in at least one of the pair of the electrodes, so it is possible to cause the lines of electric force, which describe the electric field that is generated when the voltage is applied to the pair of the electrodes, to be distributed such that they are locally concentrated. Accordingly, the present apparatus is able to move the liquid droplet smoothly even if the voltage that is applied by the electric field generating portion is reduced.

In the exogenous substance transfer apparatus in the first aspect, the gap between the pair of the electrodes may be not greater than one centimeter. The electric field generating portion may be configured to move the liquid droplet that is formed between the pair of the electrodes back and forth between the pair of the electrodes a plurality of times by repeating a cycle in which the electric field generating portion causes the liquid droplet to move toward the opposite polarity electrode and causes the liquid droplet to reverse its direction of movement by causing the liquid droplet to come into contact with the opposite polarity electrode.

The exogenous substance transfer apparatus in this case is able to exert the electrical action on the liquid droplet a plurality of times. Accordingly, by exerting a sufficient amount of the electrical action on the liquid droplet, the present apparatus is able to introduce the exogenous substance into the cell more reliably and to improve the transfection efficiency of the exogenous substance.

In the exogenous substance transfer apparatus in the first aspect, each of the at least one storage vessel may include a bottom face portion. The insulating liquid may have a lower specific gravity than that of the cell suspension liquid and may have a viscosity such that the position of the liquid droplet when the application of the direct current voltage by the electric field generating portion is terminated is a position that is between the bottom face portion and the surface of the insulating liquid.

Contamination within the storage vessel is often due to the substances that have been put into the storage vessel remaining within the storage vessel. In the present apparatus, the cell suspension liquid that is put into the storage vessel forms the liquid droplet, and the cell and the exogenous substance are encapsulated in the interior of the liquid droplet, so the cell and the exogenous substance tend not to spread through the entire storage vessel. Furthermore, when the liquid droplet is recovered after the applying of the voltage by the electric field generating portion has been terminated, for example, in order to avoid mixing the insulating liquid into the liquid droplet, it is enough to recover an amount of the liquid droplet that is less than the amount of the cell suspension liquid that was supplied to the storage vessel. In that case, a portion of the supplied cell suspension liquid remains in the storage vessel, but due to the difference in the specific gravities of the cell suspension liquid and the insulating liquid, the remaining cell suspension liquid sinks to the bottom face portion of the storage vessel, where it accumulates separately from the insulating liquid. In a case where the processing is performed using a new liquid droplet, the new liquid droplet will be located between the bottom face portion of the storage vessel and the surface of insulating liquid when the applying of the voltage is terminated. Therefore, in the present apparatus, the mixing of the new liquid droplet with the old cell suspension liquid that has accumulated on the bottom face portion of the storage vessel is avoided by recovering the new liquid droplet from above the storage vessel. According to the present apparatus, a strictly high-precision recovery operation is not necessary in order to avoid the mixing of the insulating liquid into the recovered cell suspension liquid. Therefore, in the present apparatus, contamination of the cell into which the exogenous substance is introduced can be inhibited more reliably than in the known electroporation apparatus, even if the processing is performed a plurality of times in the same storage vessel.

In the exogenous substance transfer apparatus in the first aspect, the at least one storage vessel may be a plurality of the storage vessels arrayed in parallel. The opening portion may be formed in a top face of each one of the plurality of the storage vessels. One of the electrode portion may be provided in each one of the plurality of the storage vessels. Each one of the pair of the electrodes may extend to at least the opening portion. The exogenous substance transfer apparatus may further include a first connecting portion and a second connecting portion. The first connecting portion electrically connects to one of the pair of the electrodes in the opening portion of each one of the plurality of the storage vessels. The second connecting portion electrically connects to the other of the pair of the electrodes in the opening portion of each one of the plurality of the storage vessels. The electric field generating portion may apply the direct current voltage to the one electrode portion in each one of the plurality of the storage vessels through the first connecting portion and the second connecting portion.

The exogenous substance transfer apparatus in this case is able to perform the processing in a plurality of the storage vessels in parallel. If the storage vessels are formed from an insulating material, almost no electric current flows to the storage vessels, so the present apparatus is able to ensure safety even if the operation of applying the voltage is performed for the plurality of the storage vessels simultaneously. Therefore, the present apparatus is able to perform the processing that introduces the exogenous substance into the cell in parallel in all of the storage vessels, maintaining safety all the while.

In the exogenous substance transfer apparatus in the first aspect, each one of the at least one storage vessel may contain a plurality of the electrode portions, which are disposed with gaps between each of the plurality of the electrode portions. Each one of the pair of the electrodes extends to at least the opening portion. The exogenous substance transfer apparatus may further include a first connecting portion and a second connecting portion. The first connecting portion electrically connects to one of the pair of the electrodes in the opening portion of each one of the at least one storage vessel. The second connecting portion electrically connects to the other of the pair of the electrodes in the opening portion of each one of the at least one storage vessel. The electric field generating portion may apply the direct current voltage to the plurality of the electrode portion in each one of the at least one storage vessel through the first connecting portion and the second connecting portion.

The exogenous substance transfer apparatus in this case is able to perform a plurality of processes in a single storage vessel. If the storage vessel is formed from an insulating material, almost no electric current flows to the storage vessel, so the present apparatus is able to ensure safety even if the operation of applying the voltage is performed simultaneously for the plurality of the electrode portions that are provided in the single storage vessel. Therefore, the present apparatus is able to perform the processing that introduces the exogenous substance into the cell in parallel for all of the electrode portions, maintaining safety all the while.

According to a second aspect of the present invention, a method for manufacturing an exogenous substance-bearing cell that includes a first process and a second process is provided. The first process, by supplying a cell suspension liquid that contains a cell and at least one type of exogenous substance to an insulating liquid that is stored in a storage vessel and is not capable of being mixed with the cell suspension liquid, forms a liquid droplet in the insulating liquid. The second process that introduces the at least one type of into the cell in the liquid droplet by applying a direct current voltage for a specified length of time to a pair of electrodes that are provided on both sides of the liquid droplet that was formed in the first process. The pair of the electrodes extends in a direction that is intersectional to the surface of the insulating liquid. The applying of the direct current voltage causes the liquid droplet to move back and forth between one and the other of the pair of the electrodes and to come into contact with the pair of the electrodes.

According to the method for manufacturing the exogenous substance-bearing cell in the second aspect, the exogenous substance can be introduced into the cell with a good transfection efficiency, and a good survival rate can be achieved for the cell after the exogenous substance is introduced. According to the manufacturing method that is described above, the amount of the cell suspension liquid that is necessary for the processing is not prescribed by the volume of the storage vessel and needs only to be an amount that forms a minute liquid droplet. Therefore, according to the present manufacturing method, in a case where a genetic transformation is carried out by introducing an exogenous gene (DNA) into an animal cell, for example, the amount that is used of the cell suspension liquid that contains the exogenous gene and the animal cell can be reduced to far below what is used by the known techniques, making it possible to dramatically reduce the number of cells and the amount of the exogenous gene that are required.

In the method for manufacturing an exogenous substance-bearing cell in the second aspect, the second process may be a process that introduces the at least one type of exogenous substance into a nucleus of the cell.

According to the method for manufacturing the exogenous substance-bearing cell in this case, the second process introduces the exogenous substance into the nucleus of the cell. The present manufacturing method can introduce the exogenous substance into the nucleus of the cell more easily and reliably than can the known methods for introducing an exogenous substance.

In the method for manufacturing an exogenous substance-bearing cell in the second aspect, the first process may be a process that forms the liquid droplet by supplying to the insulating liquid a cell suspension liquid that contains a plurality of types of exogenous substances. The second process may be a process that introduces the plurality of types of the exogenous substances into the cell by applying the direct current voltage for the specified length of time.

According to the method for manufacturing the exogenous substance-bearing cell in the second aspect, the plurality of types of the exogenous substances can be introduced into the cell in a single set of the second process, and a good survival rate can be achieved for the cell into which the plurality of types of the exogenous substances have been introduced with superior transfection efficiency.

In the method for manufacturing an exogenous substance-bearing cell in the second aspect, the cell that is used in the first process may be at least one of a human somatic cell and a somatic cell from an animal other than a human.

According to the method for manufacturing the exogenous sub stance-bearing cell in this case, the exogenous substance can be introduced easily, at low cost, and with superior transfection efficiency into at least one of a human somatic cell and a somatic cell from an animal other than a human, and a good survival rate can be achieved for the genetically transformed somatic cell.

In the method for manufacturing an exogenous substance-bearing cell in the second aspect, the insulating liquid may include a first insulating liquid and a second insulating liquid. A specific gravity of the second insulating liquid is less than that of the first insulating liquid. The method for manufacturing the exogenous substance-bearing cell may further includes a pouring process. The pouring process, prior to the first process, may pours the first insulating liquid and the second insulating liquid into the storage vessel, causing a layer of the second insulating liquid to form above a layer of the first insulating liquid. The first process may be a process that forms the liquid droplet within the second insulating liquid. The second process may be a process that moves the liquid droplet back and forth within the second insulating liquid by applying the direct current voltage to the pair of the electrodes for the specified length of time.

According to the method for manufacturing the exogenous substance-bearing cell in this case, the liquid droplet can be moved smoothly within the second insulating liquid. The present manufacturing method is able to introduce the exogenous substance into the cell with a transfection efficiency that is superior to the transfection efficiency in a case where the liquid droplet does not move smoothly.

In the method for manufacturing an exogenous substance-bearing cell in the second aspect, the method for manufacturing the exogenous substance-bearing cell may further include a preparation process. The preparation process, prior to the first process, adjusts the cell suspension liquid that contains the cell and the at least one type of exogenous substance suspended in a phosphate-buffered solution. The first process may be a process that pours the cell suspension liquid adjusted in the preparation process into the container to form the liquid droplet. The method for manufacturing the exogenous substance-bearing cell in this case achieves a better transfection efficiency for the exogenous substance than is the case when the cell and at least one of the exogenous substance are suspended in a liquid culture medium for culturing the cell.

In the method for manufacturing an exogenous substance-bearing cell in the second aspect, the insulating liquid may have a lower specific gravity than that of the cell suspension liquid and has a viscosity such that the position of the liquid droplet when the application of the direct current voltage by the electric field generating portion is terminated is a position that is between the bottom face portion and the surface of the insulating liquid. The method for manufacturing the exogenous substance-bearing cell in this case achieves a better transfection efficiency for the exogenous substance than is the case where the position of the liquid droplet when the applying of the direct current voltage for the specified length of the time is terminated is a position where the liquid droplet is in contact with the bottom face portion of the storage vessel.

According to a third aspect of the present invention, an exogenous substance transfer apparatus that introduces an exogenous substance into a cell from outside the cell by electrical action is provided, The exogenous substance transfer apparatus includes an electrode portion, an electric field generating portion. The electrode portion includes a pair of electrodes. In a case where the pair of electrodes are disposed such that they are separated from one another inside a storage vessel that has an opening portion through which a substance can be supplied from the outside, the pair of electrodes expends in a direction that is intersectional to the horizontal plane. The pair of electrodes is formed into shapes that, when a direct current voltage is applied, cause a plurality of virtual lines of electric force to be distributed such that they are locally concentrated. The electric field generating portion is configured to generate an electric field by applying a direct current voltage to the electrode portion for a specified length of time. The electric field generating portion is configured, when applying the direct current voltage to the electrode portion, to cause a liquid droplet of a cell suspension liquid to move toward an opposite polarity electrode and to cause the liquid droplet to reverse its direction of movement by causing the liquid droplet to come into contact with the opposite polarity electrode. The opposite polarity electrode is one of the pair of the electrodes whose polarity is an opposite of a polarity of the liquid droplet. The direct current voltage is applied in a state in which the cell suspension liquid has been supplied between the pair of the electrodes in each of the storage vessel storing an insulating liquid to form the liquid droplet in the insulating liquid. The cell suspension liquid contains an exogenous substance and a cell. The cell suspension liquid is not capable of being mixed with the insulating liquid. The liquid droplet has a diameter smaller than a gap between the pair of the electrodes.

According to the exogenous substance transfer apparatus in the third aspect, the using of the pair of the electrodes that are disposed within the storage vessel such that they are separated from one another demonstrates the same sort of effects as were demonstrated by the exogenous substance transfer apparatus of the first aspect.

DESCRIPTION OF EMBODIMENTS

The exemplary embodiments of the present invention will be explained with reference to the drawings. First, an exogenous substance transfer apparatus 1 according to a first embodiment of the present invention will be explained with reference to FIGS. 1 and 2.

The exogenous substance transfer apparatus 1 (hereinafter also called the apparatus 1) is an apparatus that is configured to introduce a specific exogenous substance into a target cell by electrical action. The target cell is a cell that is the object of the transfection of the exogenous substance. The apparatus 1 does not require a pulse generator. Furthermore, the apparatus 1 is configured such that the amount of a liquid suspension of cells (the number of the target cells and the amount of the exogenous substance) that is required for a single round of processing can be made extremely small.

Figure 1:
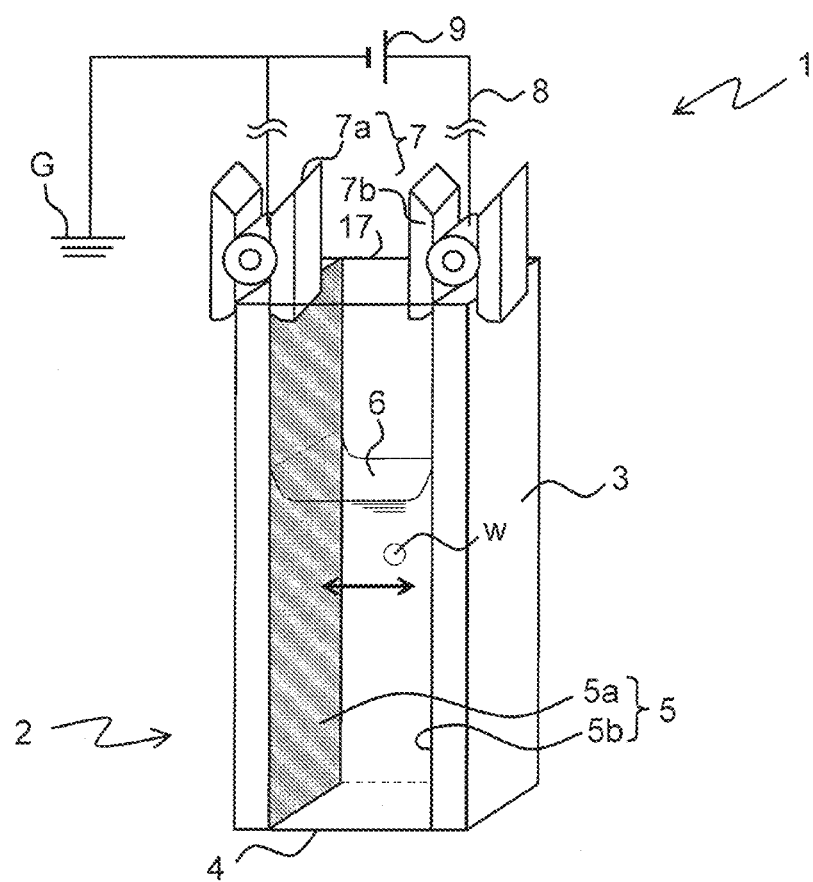
FIG. 1 is a drawing that shows an outline of an exogenous substance transfer apparatus 1 in a first embodiment.

Specifically, as shown in FIG. 1, the exogenous substance transfer apparatus 1 is provided with a container 2, which contains an insulating oil 6, an electrode portion 5, and a power supply 9. The overall form of the container 2 is substantially a three-dimensional rectangle, and it has a bottom face portion 4 and four side walls 3 that are provided such that they extend upward from the perimeter of the bottom face portion 4. An opening portion 17 is formed in a top face of the container 2. The apparatus 1 is able to contain a liquid in the interior of the container 2. The container 2 is formed from an insulating material, such as plastic, glass, ceramic, or the like, for example. The shape of the container 2 may be any shape, as long as it is a shape that can contain a liquid. In the present embodiment, a plastic container in which the bottom face portion 4 is a 1-centimeter square and the side walls 3 are 4.5 centimeters high (for example, a 3-milliliter spectrophotometer cuvette) is used as the container 2.

The electrode portion 5 is formed by affixing electrically conductive aluminum tapes with a thickness of 0.1 millimeters to the inside faces of the side walls 3 on the left and right sides of the container 2. The electrode portion 5 includes a left-right pair of electrodes 5a, 5b. The electrodes 5a, 5b are formed into rectangular shapes that have almost the same dimensions as the inside faces of the side walls 3 and that cover almost the entire inside faces of the left and right side walls 3, respectively. The upper ends of the electrodes 5a, 5b extend to the opening portion 17 of the container 2. Therefore, the electrodes 5a, 5b are disposed opposite one another inside the container 2, separated by a gap of approximately 1 centimeter, in a state in which they extend vertically (that is, in a direction that is intersectional to the horizontal).

Metal clips 7a, 7b, which are respectively electrically connected to the electrodes 5a, 5b, respectively clamp the left and right side walls 3 close to the opening portion of the container 2. The clip 7a, which is electrically connected to the electrode 5a, is connected to the negative electrode of the power supply 9 through a conductor 8. The clip 7b, which is electrically connected to the electrode 5b, is connected to the positive electrode of the power supply 9 through the conductor 8.

The power supply 9 is a high-voltage direct current power supply. The maximum output voltage of the power supply 9 is at least 5 kilovolts. The maximum output current of the power supply 9 is at least 0.5 milliamperes. The power supply 9 is electrically connected through the conductor 8 to the electrodes 5a, 5b that are provided in the container 2. The negative side of the power supply 9 is grounded. When a voltage from the power supply 9 is applied, an electric field is generated between the pair of the electrodes 5a, 5b that are affixed to the inside faces of the container 2. The power supply 9 is provided with a switch for switching the supply of voltage on and off, a dial for adjusting the voltage that is supplied, and a timer for setting a desired time, although these are not shown in the drawings. The apparatus 1 is configured such that, when an operator has used the dial to set the supplied voltage and has set the timer to the desired time, the switch turns on, and the supply of voltage starts, and when the time that was set on the timer has elapsed, the switch turns off, and the voltage output stops.

The voltage that is supplied from power supply 9 is varied according to the shape and the capacity of the container 2 that is used. When the strength of the electric field is too low, a liquid droplet W does not move back and forth between the electrodes 5a, 5b, and when the strength of the electric field is too great, the liquid droplet W deforms and connects the electrodes 5a, 5b, or the liquid droplet W is destroyed. Therefore, the applied voltage is regulated such that the strength of the electric field that is formed in the container 2 is in the range of 1 to several kilovolts per centimeter.

When the processing is performed that introduces an exogenous substance such as gene or the like into the target cell, a cell suspension liquid (an aqueous hydrophilic liquid that forms droplets) that contains the target cells and the exogenous substance is supplied through the opening portion 17 of the container 2. The cell suspension liquid is supplied to the container 2 in an amount that is regulated such that the liquid droplet W that is formed by the cell suspension does not come into contact with both of the electrodes 5a, 5b at the same time. In the present embodiment, the amount of the cell suspension liquid that is supplied in one round is approximately 2 to 5 microliters. The cell suspension liquid is an aqueous liquid and is not capable of being mixed with the oil 6 that is contained in the container 2. One of the liquid droplet W (a water-in-oil droplet) is formed in one round of supply. The liquid droplet W that is formed is disposed between the electrodes 5a, 5b. As will be described in detail later, when the voltage is supplied from the power supply 9 to the electrodes 5a, 5b, the exogenous substance is introduced into the target cell in the liquid droplet W by electrical action.

The oil 6 that is contained in the container 2 is a substance that is in a separate phase from water and is more hydrophobic than the cell suspension liquid (water), it is liquid at close to room temperature, and it has an insulating property. An alkane-type mineral oil that is derived from petroleum, an insulating oil whose main constituent is alkyl benzene, an insulating oil whose main constituent is polybutene, an insulating oil whose main constituent is alkyl naphthalene, an insulating oil whose main constituent is alkyl diphenylalkane, silicone oil, or the like, for example, may be used as the oil 6. Any one of these oils or a mixture of a plurality of types of oil may be used as the oil 6. The oil 6 is not limited to the examples cited above, and it needs only to be a hydrophobic liquid that is insulating and is not capable of being mixed with the cell suspension liquid.

An insulating oil with a lower specific gravity than the liquid droplet W is chosen as the oil 6, in order to dispose the liquid droplet W within the oil 6. Further, the liquid droplet W settles out of the oil 6, but the insulating oil that is chosen as the oil 6 has a suitable viscosity, such that the liquid droplet W settles out comparatively slowly. Preferably, the insulating oil that is chosen as the oil 6 will have a viscosity that controls the settling velocity of the liquid droplet W, such that the liquid droplet W will be positioned higher than the bottom face portion 4 even at the point when the application of the voltage by the power supply 9 is terminated. Strictly speaking, the specific gravity of the liquid droplet W is the specific gravity of the cell suspension liquid, but the amount of the cell suspension liquid that is occupied by the cells and the exogenous substance is insignificant. Therefore, simply put, the specific gravity of the aqueous liquid that is used as the solvent (the dispersion medium) (a solution such as a buffer solution or the like that will be described later), or the specific gravity of water, may be substituted for the specific gravity of the liquid droplet W.

As explained above, the cell suspension liquid (the liquid droplet W) and the oil 6 do not mix. Therefore, if the liquid droplet W is recovered after the electrical processing to introduce the exogenous substance has been performed by the apparatus 1, the possibility that contamination will occur in a new liquid droplet is inhibited, even if a new liquid droplet is then formed in the container 2 and the introducing of the exogenous substance is performed. If the operator uses the oil 6 after passing it through a sterilizing filter and performs a series of operations in a clean bench, the occurrence of contamination can be inhibited. Preferably, it is desirable for the oil 6 not to be mixed into the liquid droplet W when the liquid droplet W is recovered. Ideally, the amount of the cell suspension liquid that is recovered will be exactly the same as the amount that was supplied. In a case where it is difficult to perform an operation that will recover exactly the same amount of the cell suspension liquid as the amount that was supplied, the operator may avoid mixing of the oil 6 into the liquid droplet W by recovering an amount of the liquid droplet W that is only slightly smaller than the amount that was supplied. In that case, some of the cell suspension liquid will remain within the container 2, but in the apparatus 1, the remaining cell suspension liquid settles out and stays on the bottom face portion 4, due to the difference in specific gravity between the cell suspension liquid and the oil 6. Therefore, the viscosity of the oil 6 is regulated such that the liquid droplet W will be positioned higher than the bottom face portion 4 at the point when the electrical processing is terminated, and the cell suspension liquid (that is, the liquid droplet W) may be recovered using a pipette or the like through the opening portion 17 in the top face of the container 2. If that is done, none of the remaining old cell suspension liquid will be in the position where the electrical processing of the liquid droplet W is performed in the container 2 or in the position where the liquid droplet W is recovered. Therefore, even if the cell suspension liquid is newly supplied to the same container 2, contamination will not occur in a new liquid droplet.

Examples of the exogenous substance include substances that can be introduced by the existing electroporation method, such as various types of bioactive substances that cannot pass through the cell membrane in its normal state, chemical agents, therapeutic agents, nucleic acid substances, peptides, proteins, and the like, for example. The nucleic acid substances may include DNA molecules, RNA (including siRNA) molecules, viral DNA, plasmid DNA, oligonucleotides (antisense oligonucleotides, aptamers), and peptide nucleic acid. The DNA that is chosen as desired is DNA that includes the nucleic acid sequences that are to be introduced into the target cell, and DNA that is designed for a specific purpose is used, such as full-length sequences of genes (cDNA sequences, genomic sequences), partial sequences, regulatory regions, spacer regions, mutated sequences, and the like, for example. Polypeptides that are encoded by the DNA can be produced by the cells into which the DNA has been introduced.

The type of the target cell is not particularly limited, and various types of cells can be used as the target cell. For example, a plant cell, an animal cell, including a human cell, a bacterium, and the like can be used as the target cell. The apparatus 1 is capable of introducing a exogenous substance into any cell into which an exogenous substance can be introduced by the known electroporation method. Examples of a cell into which an exogenous substance can be introduced by the known electroporation method include, among animal-derived cells, either human or non-human, a somatic cell, an embryonic cell (ES cell), a fertilized ovum, and a fetal tissue cell. With the apparatus 1, exogenous genes are introduced with a better transfection efficiency than by the known electroporation method, and a better survival rate is achieved. Therefore, the apparatus 1 is useful as a method for the genetic transformation of a cell into which an exogenous substance can be introduced by the known electroporation method. In particular, the apparatus 1 achieves a good transfection efficiency and a good survival rate, even in a case where an exogenous substance (an exogenous gene) is introduced into a neuron-like cell line that has been differentiated from an animal-derived neuron-like cell by the addition of a chemical agent (retinoic acid). The apparatus 1 can also introduce an exogenous substance (an exogenous gene) into a first-generation mouse hippocampal cell by the same method. Therefore, a good gene transfection efficiency and a good cell survival rate can be achieved in a case where the apparatus 1 is used for the genetic transformation of a neuron, which until now has had a problem with the survival rate after the transfection of an exogenous gene. The apparatus 1 is able to introduce an exogenous substance regardless whether the target cell is an adherent cell or a floating cell.

The exogenous substance and the target cell are suspended in an aqueous solution. The aqueous solution is not particularly limited, as long as it is a hydrophilic solution that is not capable of being mixed with the oil 6 and does not adversely affect the exogenous substance and the target cell. For example, a buffer solution that can be used with the ordinary electroporation method, such as a phosphate-buffered saline solution (hereinafter simply called the PBS buffer solution), a 4-(2-hydroxyethyl)-1-piperazineethanesulfonic acid solution (HEPES) or the like, as well as an ordinary buffer solution, are used as the aqueous solution. If the target cell is an animal cell, a liquid culture medium that can be used to culture animal cells (for example, the MEM medium, the DMEM medium, the Opti-MEM medium, the α-MEM medium, the RPMI-1640 medium, the DMEM/F-12 medium, the Williams medium, the ES medium, or the like) can be used as the aqueous solution. With these liquid culture media, a low serum concentration is preferable from the standpoint of transfection efficiency, and a serum-free medium is particularly desirable. Generally, a liquid culture medium that does not contain an antibiotic is preferable as the aqueous solution. Serum and an antibacterial agent may be added after the processing by the apparatus 1 that introduces the exogenous substance. From the standpoint of the transfection efficiency and the effects on the cell, it is preferable for a phosphate-buffered solution to be used as the aqueous solution. Considering the effects on the cell, it is best to control the pH of the aqueous solution, and a pH in the range of 7.0 to 7.6 is preferable.

The amount of the exogenous substance that is contained in the solution may be any amount that enables the known electroporation method to be performed. From the standpoint of the survival rate of target cells and the transfection efficiency of the exogenous substance, it is preferable for the concentration of the exogenous substance in the cell suspension liquid to be in the range of 0.1 to 3 micrograms per microliter, and even better for the concentration to be in the range of 0.2 to 3 micrograms per microliter, with the concentration being adjusted appropriately for the exogenous substance. The exogenous substances that are contained in the cell suspension liquid are not limited to one type, and a plurality of types of exogenous substances may also be contained in the cell suspension liquid. Thus the apparatus 1 can introduce a plurality of types of exogenous genes, for example, into the target cell in a single round of processing.

Using the apparatus 1, the operator can introduce a plurality of types of exogenous genes into the target cell by the simple operation of including the target cell and the plurality of types of exogenous genes in the cell suspension liquid as described above. Using the apparatus 1, a plurality of types of exogenous genes can be introduced into a somatic cell with good transfection efficiency, with an excellent survival rate among the target cells after the processing. Therefore, the apparatus 1 is able to introduce four initialized genes (the so-called Yamanaka factors Oct3/4, Sox2, and Klf4, and cMyc) into a differentiated cell such as a human fibroblast or the like in a single round of processing. In other words, the apparatus 1 is preferably applied to the manufacturing of induced pluripotent stem cells (iPS cells) that have pluripotency like that of embryonic stem cells (ES cells) and a capacity for self-renewal that can maintain pluripotency even through mitotic proliferation. The apparatus 1 can also be used to introduce genes for induced pluripotent stem cells in order to further differentiate a newly differentiated cell. The apparatus 1 is also able to introduce an exogenous gene that is contained in the cell suspension liquid not only into the target cell cytoplasm, but also into the cell nucleus. Therefore, by introducing the exogenous gene into the nucleus of the target cell, the apparatus 1 is able to make it more probable that the exogenous gene that has been introduced into the target cell will be carried over into the next generation of the target cells than would be the case with an exogenous gene that is introduced into the cytoplasm of the target cell.

The apparatus 1 is able to perform the introducing of the exogenous substance into the target cell within the liquid droplet W of several microliters that is formed in the oil 6, so as long as the number of the target cells that are contained within the liquid droplet W is in the range of $10^3$ to $10^4$ cells, the number is sufficient to meet the requirements of the processing. Therefore, the apparatus 1 is able to genetically transform a rare sample that has been harvested from a human subject (a minute amount of the target cells) with high efficiency.

When the direct current voltage is applied to the container 2 by the power supply 9, a direct current electric field is formed between the pair of the electrodes 5a, 5b. The liquid that is contained inside the container 2 is the insulating oil 6, so the amount of current that flows through the oil 6 is tiny. The liquid droplet W that is present in the oil 6 is an aqueous solution, so when the direct current electric field of several kilovolts per centimeter is generated between the electrodes 5a, 5b, an electrical charge is induced on the surface of the liquid droplet W. The electrically charged liquid droplet W moves toward the electrode in the pair of the electrodes 5a, 5b that has a polarity that is different from the polarity of the liquid droplet W (the opposite polarity electrode) and comes into contact with the opposite polarity electrode, which is disposed in the direction in which the liquid droplet W moves. The polarity of the liquid droplet W thus switches to the opposite polarity, causing the direction in which the liquid droplet W moves to reverse, such that the liquid droplet W moves toward the electrode that is in the opposite direction.

The length of time that the direct current voltage is applied is such that a good transfection efficiency for the exogenous substance and a good survival rate for the target cells can both be achieved, for example, 10 seconds to 1 hour, or preferably, 30 seconds to 15 minutes. From the standpoint of the height of the container 2 and the viscosity of the oil 6 (the settling velocity of the liquid droplet W), that is, considering that the liquid droplet W must be positioned higher than the bottom face portion 4 even at the point when the application of the voltage by the power supply 9 is terminated, it is even more preferable for the length of time that the direct current voltage is applied to be 30 seconds to 1 minute.

Figure 2:
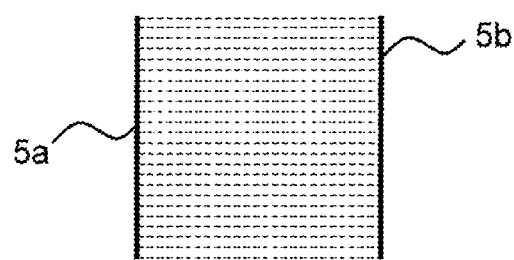
FIG. 2 is a plan view that shows, as broken lines, lines of electric force in an electrical field that arises within the exogenous substance transfer apparatus 1.

Lines of electric force that describe the electric field that is generated between the electrodes 5a, 5b in the apparatus 1 are shown in a plan view as broken lines in FIG. 2. The electrodes 5a, 5b are disposed opposite one another, extending parallel to the vertical direction, which is orthogonal to the horizontal direction, and they are formed to have the same width, so the lines of electric force are drawn at right angles to the electrodes 5a, 5b (that is, in the horizontal direction) and are evenly distributed. The liquid droplet W moves between the electrodes 5a, 5b in the direction in which the lines of electric force extend. The electric field acts on the liquid droplet W for as long as the direct current voltage is supplied from the power supply 9. Therefore, the liquid droplet W repeatedly moves back and forth between the electrodes 5a, 5b and comes into contact with the electrode portion 5 a plurality of times. For example, in a case where a pair of electrodes are provided along a bottom face that extends in the horizontal direction, the liquid droplet W, instead of moving along the bottom face, would be bound between the pair of the electrodes and would move along parabolic lines of electric force that bulge upward toward the surface of the oil 6. Therefore, the direction of electrical attraction when the liquid droplet W is in contact with an electrode would be the same as the direction of gravity. In contrast, in the apparatus 1, the electric field is generated such that the lines of electric force extend in the horizontal direction, and the electrode portion 5 is formed on the side walls 3 of the container 2, so the direction of electrical attraction when the liquid droplet W is in contact with the electrode portion 5 does not match the direction of gravity. Therefore, the apparatus 1 can prevent the movement of the liquid droplet W from stopping when the liquid droplet W is in contact with the electrode portion 5, and can move the liquid droplet W back and forth between the electrodes in a more stable manner than would be the case if a pair of electrodes were formed along a bottom face that extends in the horizontal direction. In a case where the liquid droplet W was stopped while in contact with an electrode, the apparatus 1 could cause the liquid droplet W to separate from the electrode by increasing the applied voltage, for example. However, in that case, there would be a strong possibility that the liquid droplet W would burst. If the liquid droplet W were to burst, it would be difficult to recover the liquid droplets from the oil 6, and the interior of the container 2 would be noticeably contaminated by the broken-down liquid droplets as a result. Moving the liquid droplet W smoothly while keeping the applied voltage as low as possible, as the apparatus 1 does, is extremely important from the standpoint of not bursting the liquid droplet W within the oil 6.

When the liquid droplet W is in contact with the electrode portion 5, the electrical charge is thought to move over the surface of the liquid droplet W. At this time, a locally strong electric field is thought to be formed close to the surface of the liquid droplet W, and it is presumed that the action of the electric field causes minute holes to be transiently formed in the cell membrane, through which the exogenous substance is introduced into the target cell.

As explained above, according to the exogenous substance transfer apparatus 1 in the first embodiment, an exogenous substance can be introduced into a target cell by electrical action with good transfection efficiency. Because the apparatus 1 utilizes electrical action, it is able to reduce the running cost in comparison to a chemical technique, without requiring a special reagent. Furthermore, the apparatus 1 is able to produce exogenous substance-bearing cells with a good survival rate, without any concern about carcinogenesis or the like that is due to toxicity to the cells or antigenicity, as happens with biological techniques that use a virus. Moreover, with the apparatus 1, the pulse generator that is essential for the general-purpose electroporation apparatus is not needed. Because the configuration of the apparatus 1 is simple, the apparatus 1 is manufactured at a low cost.

Furthermore, the apparatus 1 is able to limit the amount of the cell suspension liquid that is necessary for introducing a gene into the target cell to just several microliters. Thus, in comparison with the known methods, the apparatus 1 is able to dramatically reduce the number of the target cells and the amount of the DNA (the exogenous genes) that are required. Therefore, the apparatus 1 is extremely useful as an apparatus for the genetic transformation of a rare sample that has been harvested from a human subject, for example.

Figure 3:
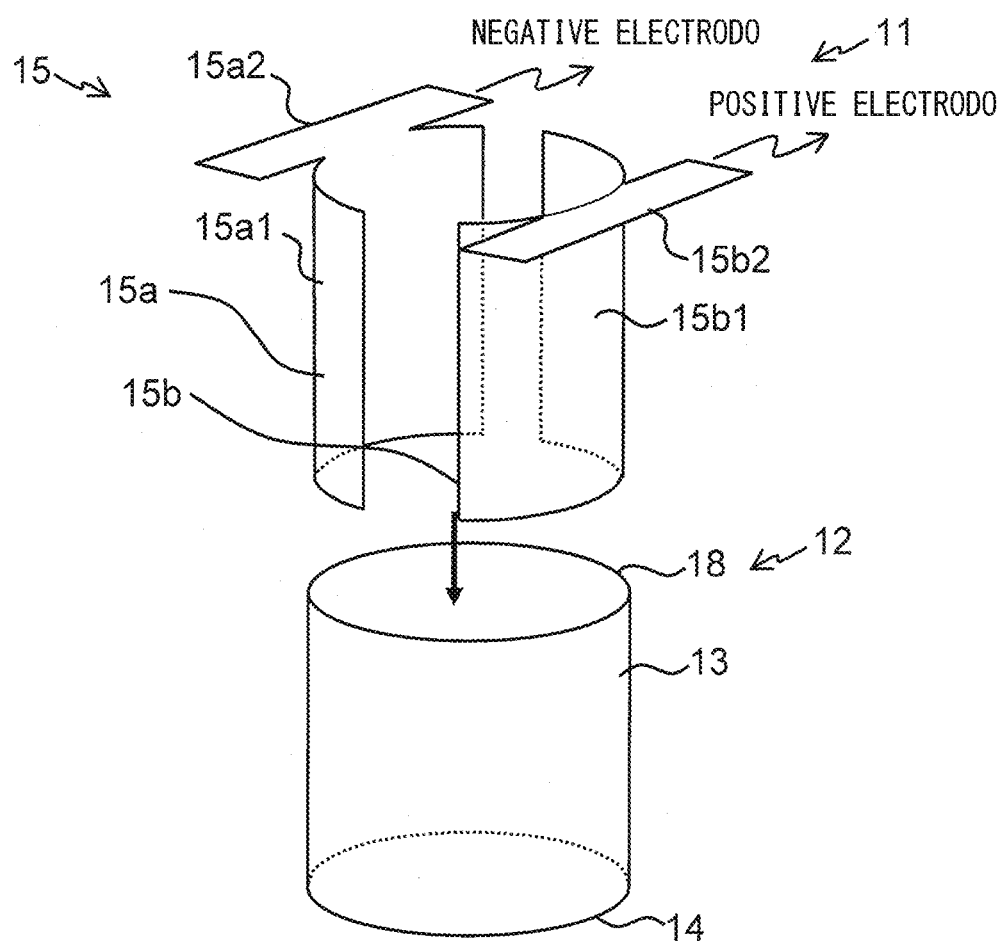
FIG. 3 is an exterior schematic view that shows an outline of a container 12 and an electrode structure 15 of an exogenous substance transfer apparatus 11 in a second embodiment.

An exogenous substance transfer apparatus 11 (hereinafter called the apparatus 11) in a second embodiment will be explained with reference to FIG. 3. In the first embodiment, the apparatus 1 is provided with the container 2, whose overall form is substantially a three-dimensional rectangle, and the rectangular electrodes 5a, 5b on the inside faces of the left and right side walls 3 of the container 2. In contrast, in the apparatus 11 in the second embodiment, a container 12, which is a storage vessel, is formed into a cylindrical shape in the apparatus 1, and electrodes 15a, 15b that are curved surfaces are disposed along the inner circumference of the container 12. The parts that are the same as in the first embodiment are assigned the same reference numerals, and explanations of them will hereinafter be omitted. The conductor 8 and the power supply 9 have been omitted from FIG. 3.

The container 12 is a storage vessel that is formed from the same sort of insulating material as is the container 2 in the first embodiment. The container 12 is able to contain the insulating oil 6. The container 12 is formed into a cylindrical shape that has a bottom, and it includes a circular bottom face portion 14, a side wall 13 that is provided such that it extends upward from the perimeter of the bottom face portion 14, and an opening portion 18 that is formed in a top face of the container 12. In the present embodiment, the container 12 is formed with an inside diameter of 8 millimeters and a height of 10 millimeters.

An electrode portion 15 that is provided in the container 12 includes the left-right pair of the electrodes 15a, 15b. Each one of the pair of the electrodes 15a, 15b has the same shape.

The electrodes 15a, 15b are respectively provided with sheet portions 15a1, 15b1, which are rectangular sheets that are formed into curved surfaces, and with connecting portions 15a2, 15b2. The connecting portions 15a2, 15b2 are respectively connected to the top edges of the sheet portions 15a1, 15b1. The heights of the sheet portions 15a1, 15b1 are substantially the same as the height of the side wall 13. The sheet portions 15a1, 15b1 are square members whose widths are less than half of the inner circumference of the container 12, and they are shaped such that their curvatures follow the inner circumference of the container 12. The shapes of horizontal cross sections of the sheet portions 15a1, 15b1 are circular arcs. The connecting portions 15a2, 15b2 are formed into rectangular shapes of a size that can be clamped by clips 7, and they are provided on the top edges of the sheet portions 15a1, 15b1, respectively, extending in directions in which they are bent at right angles to the sheet portions 15a1, 15b1.

The electrodes 15a, 15b are each inserted into the container 12 and are set such that the outer circumferential surfaces of sheet portions 15a1, 15b1 are in contact with the inner wall of the container 12. Therefore, the sheet portions 15a1, 15b1 are opposite one another in a state in which they extend in the up-down direction of the container 12. Both edges of the sheet portion 15a1 in the width direction are positioned such that they are separated by gaps from and do not touch both edges of the sheet portion 15b1. In the present embodiment, aluminum tape with a thickness of 0.09 millimeters and an adhesive layer on its back surface is used for the electrodes 15a, 15b. The aluminum tape is affixed by being stuck to predetermined positions inside the container 12. The electrodes may also be formed from aluminum foil or thin aluminum plates instead of from the aluminum tape. The electrodes may also be formed using other materials (for example, platinum, gold, carbon electrodes, or the like) instead of the aluminum tape, as long as the material is an electrically conductive material that can be used as an electrode. From the standpoint of moving the liquid droplet W smoothly, it is preferable for the electrodes to be formed from a material that is approximately as hydrophobic as aluminum, rather than a hydrophilic material.

The connecting portion 15a2 of the electrode 15a is a terminal, and it is connected to the negative electrode of the power supply 9 through the clips 7 and the conductor 8. The connecting portion 15b2 of the electrode 15b is a terminal of the same sort, and it is connected to the positive electrode of the power supply 9 through the clips 7 and the conductor 8.

Figure 4:
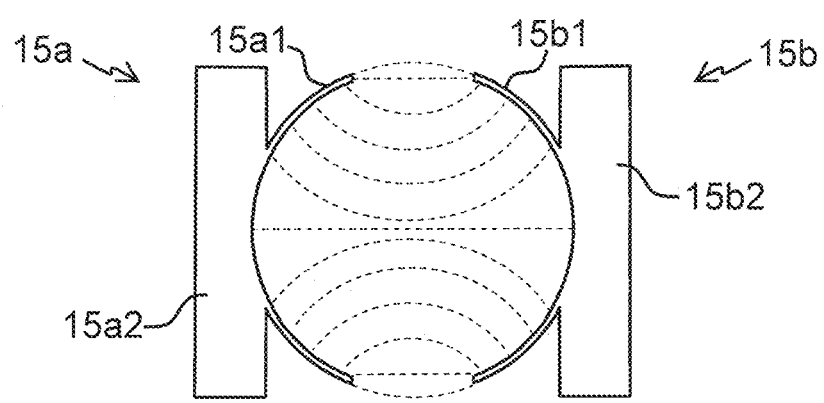
FIG. 4 is a drawing that shows, as broken lines, lines of electric force in an electrical field that can arise between electrodes 15a, 15b.

When the voltage is supplied from the power supply 9, a non-uniform electric field is formed between the electrodes 15a, 15b. Specifically, as shown by broken lines in FIG. 4, an electric field is generated between the electrodes 15a, 15b that is described by lines of electric force that are distributed by electric flux density in a plan view. The distribution of the electric flux density becomes especially dense close to the edges in the width direction of the sheet portions 15a1, 15b1 of the electrodes 15a, 15b. The edges in the width direction are the locations where the distance between the electrodes is the shortest, and the electrostatic attraction is locally strong at the edges in the width direction. The action of the locally strong electrostatic attraction makes it possible for the liquid droplet W in the container 12 to move smoothly back and forth over the shortest distance between the electrodes 15a, 15b along the lines of electric force that connect the edges in the width direction of the sheet portions 15a1, 15b1.

The apparatus 11, by forming the non-uniform electric field, is able to dramatically inhibit the phenomenon in which the liquid droplet W is in contact with the electrodes 15a, 15b and ceases to move, thereby achieving good contact and separation between the liquid droplet W and the electrodes 15a, 15b and performing the processing in a stable manner. The apparatus 11 is thus able to introduce an exogenous substance into a target cell in the liquid droplet W with better transfection efficiency than would be the case if a uniform electric field were formed between the electrodes.

In the apparatus 11 of the second embodiment, the electrode portion 15 includes the pair of the electrodes 15a, 15b, which have identical structures. The electrodes 15a, 15b are provided with sheet portions (the sheet portions 15a1, 15b1, respectively) that are curved surfaces and with connecting portions (the connecting portions 15a2, 15b2, respectively) that are connected to the sheet portions. The apparatus 11 of the second embodiment is not limited to having the electrodes that are described above, as long as the electrodes form a non-uniform electric field, and the apparatus 11 may also have electrodes like those shown in FIGS. 5 to 7, instead of the electrodes with the structure that is described above.

Figure 5:
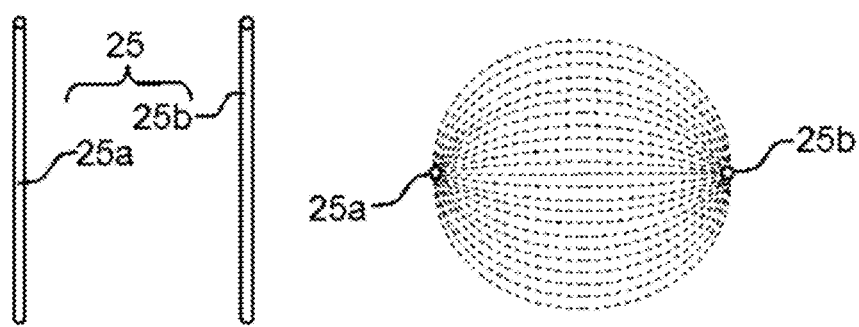
FIG. 5 is an oblique view of an electrode portion 25 that includes needle-shaped electrodes 25a, 25b, and a plan view that shows, as broken lines, lines of electric force in an electrical field that arises between the electrodes 25a, 25b.

For example, the electrode portion of the apparatus 11 may be an electrode portion 25 that includes a pair of cylindrical (needle-shaped) electrodes 25a, 25b whose diameters are sufficiently smaller than the inside diameter of the container 12, as shown in FIG. 5. The pair of the electrodes 25a, 25b are provided inside the container 12 such that their lengthwise directions extend in the up-down direction (the direction that is intersectional to the horizontal direction) in positions where they are sufficiently separated from each other along the diameter of the container 12. The electrodes 25a, 25b are formed to lengths that protrude upward from the opening portion 18 that is formed in the top face of the container 12. The ends that protrude from the opening portion 18 are clamped by the clips 7. In a case where the apparatus 11 is provided with the electrode portion 25 in FIG. 5, the apparatus 11 forms a non-uniform electric field in which the lines of electric force are concentrated in the vicinity of the electrodes 25a, 25b. The apparatus 11 is thus able to move the liquid droplet W smoothly in the same manner as in the second embodiment.

Figure 6:
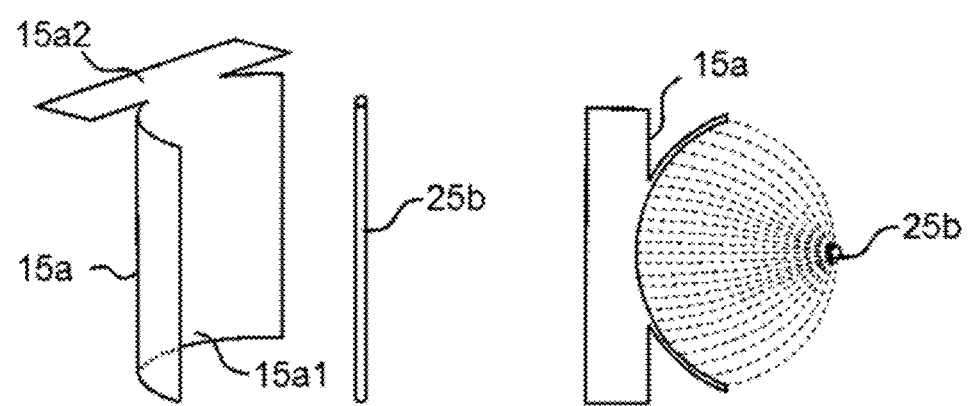
FIG. 6 is an oblique view of the electrode 15a and the needle-shaped electrode 25b, and a plan view that shows, as broken lines, lines of electric force in an electrical field that arises between the electrode 15a and the electrode 25b.

As shown in FIG. 6, a pair of electrodes may also be formed by the electrode 15a on one side in the second embodiment and the electrode 25b that is described above. In a case where the apparatus 11 is provided with the electrode 25b, a non-uniform electric field is formed in which the lines of electric force are concentrated in the vicinity of the electrodes 15a, 25b, as shown in FIG. 6, and the apparatus 11 is able to move the liquid droplet W smoothly, in the same manner as in the second embodiment.

Figure 7:
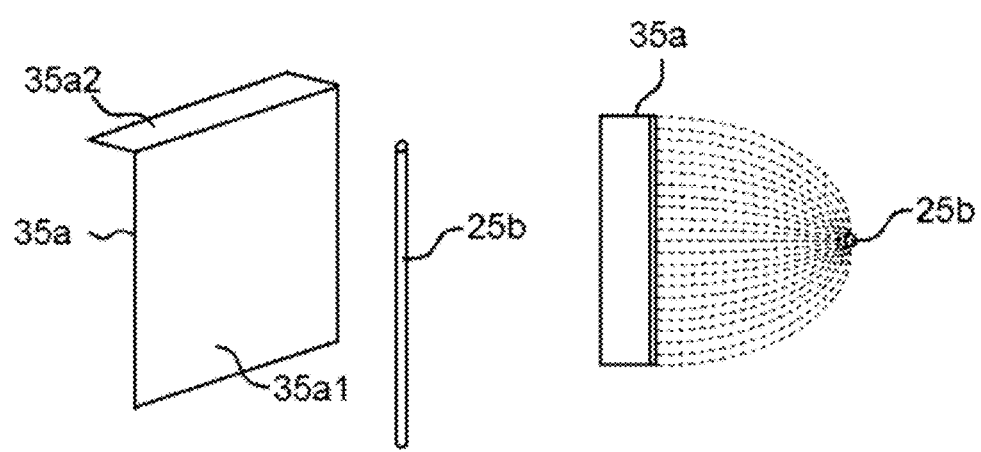
FIG. 7 is an oblique view of a plate-shaped electrode 35a and the needle-shaped electrode 25b, and a plan view that shows, as broken lines, lines of electric force in an electrical field that arises between the electrode 35a and the electrode 25b.

FIG. 7 shows a case in which a plate-shaped electrode 35a is used in which the shape of the sheet portion of the electrode 15a in FIG. 6 has been changed to a flat plate shape. In the modified example that is shown in FIG. 7, a pair of electrodes is formed by using the electrode 35a as one of the electrodes and the electrode 25b as the other electrode. The electrode 35a has a connecting portion 35a2 that extends outward (toward the opposite side from the side that faces the electrode 25b) at a 90-degree angle from a planar sheet portion 35a1. The connecting portion 35a2 is formed into a rectangular shape in a plan view, and the length of the connecting portion 35a2 in the lengthwise direction is greater than the width of the sheet portion 35a1. In a state in which an electrode portion 35 is disposed inside the container 12, the edge of the connecting portion 35a2 protrudes to the outside of the side wall 13 of the container 12. The connecting portion 35a2 is rigid and has a size that is clamped by the clips 7.

The width of the sheet portion 35a1 is less than the inside diameter of the container 12, and the height of the sheet portion 35a1 is substantially the same dimension as the inner wall height of the side walls 13 of the container 12. The electrode 25b is disposed in relation to the electrode 35a such that it is sufficiently separated from the electrode 35a, in a position where it is opposite the vicinity of the center of the width direction (the direction that is orthogonal to the up-down direction) of the electrode 35a.

In a case where the apparatus 11 is provided with the electrodes 35a, 25b that are shown in FIG. 7, the apparatus 11 forms a nom-uniform electric field in which the lines of electric force are concentrated in the vicinity of the electrode 25b. The apparatus 11 is thus able to move the liquid droplet W smoothly, in the same manner as in the second embodiment.

An exogenous substance transfer apparatus 41 (hereinafter called the apparatus 41) in a third embodiment will be explained with reference to FIGS. 8 and 9. The parts that are the same as in the second embodiment are assigned the same reference numerals, and explanations of them will hereinafter be omitted. The apparatus 41 is configured such that the processing that introduces an exogenous substance can be performed in parallel at the same time in a plurality of the containers (wells) 12.

Figure 8:
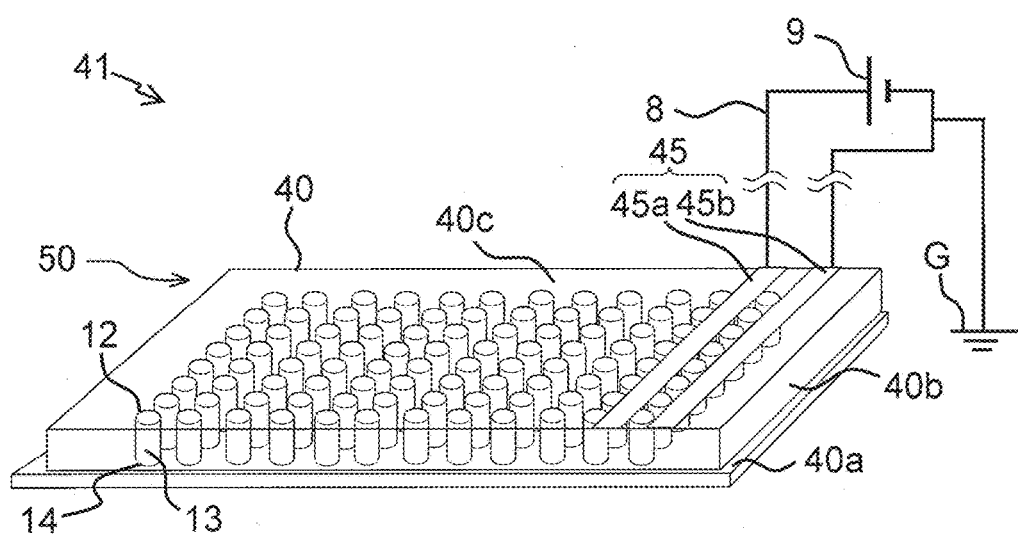
FIG. 8 is a drawing that shows an outline of an exogenous substance transfer apparatus 41 in a third embodiment.

As shown in FIG. 8, the apparatus 41 is provided with a processing container 50 that is a 96-hole cell culturing plate. The processing container 50 is provided with a support body 40, in which a rectangular frame 40a, four side wall faces 40b that extend upward from a top face of the frame 40a, and a top plate 40c that spans the top edges of the side wall faces 40b are formed into a single unit. The plurality of the containers 12 are each held by the support body 40.

Circular through-holes of the same size as the inner circumference of the container 12 are formed in the top plate 40c. The top faces of the side walls 13 of the containers 12 are joined to the bottom face of the top plate 40c in positions where the through-holes in the top plate 40c are aligned to the opening portions 18 of the containers 12 (refer to FIG. 3). The heights of the containers 12 are the same as the heights of the side wall faces 40b. The containers 12 are thus formed into a single unit with the support body 40 by being affixed to the top plate 40c in a state in which they are suspended above an installation surface of the processing container 50 by a distance that is equal to the height of the frame 40a.

Ninety-six of the containers 12 are provided in the processing container 50. The ninety-six containers 12 are arrayed in eight rows and twelve columns. The electrode portion 15 is set in each one of the containers 12. The sheet portions 15a1 of the electrodes 15a are inserted into the containers 12. The connecting portions 15a2 are placed on the top face of the top plate 40c. The height of the sheet portion 15a1 of the electrode 15a is substantially the same dimension as the height of the side wall 13 of the container 12, so the bottom edge of the sheet portion 15a1 is disposed in a position that is above the inner side of the bottom face portion 14 by a distance that is equal to the thickness of the top plate 40c. There is no particular restriction on the size of the sheet portion 15a1, as long as it is a size that can form an electric field that can move the liquid droplet W well within the container 12. The height of the sheet portion 15a1 may also be lower. The height of the sheet portion 15a1 may also be a height to which a length that is equal to the thickness of the top plate 40c has been added, such that the bottom edge of the sheet portion 15a1 reaches the bottom face portion 14. The electrode 15b is set into each one of the containers 12 in the same manner as the electrode 15a, with a specified gap between the electrode 15b and the electrode 15a. The specified gap is set using the shortest distance between the electrodes as a reference.

A plate-shaped strip portion 45, which includes a pair of long, narrow, rectangular plate-shaped strips 45a, 45b that flank a column of the containers 12, is provided in the top plate 40c. The plate-shaped strip portion 45 is formed from an electrically conductive material such as a metal or the like. The lengths of the plate-shaped strips 45a, 45b in the lengthwise direction are substantially the same dimension as the length of the top plate 40c in the width direction (the direction in which the columns of the containers 12 extend). The lengths of the plate-shaped strips 45a, 45b in the shorter direction are substantially the same dimension as the gap between adjacent columns of the containers 12. Electrical contact points with the conductor 8 are provided at the rearward ends of the plate-shaped strips 45a, 45b in FIG. 8. One of the pair of the plate-shaped strips 45a, 45b (the plate-shaped strip 45a) is connected to the positive electrode of the power supply 9 through the conductor 8, which is connected to the electrical contact point. The other of the pair of the plate-shaped strips 45a, 45b (the plate-shaped strip 45b) is connected to the negative electrode of the power supply 9 through the conductor 8, which is connected to the electrical contact point.

Figure 9:
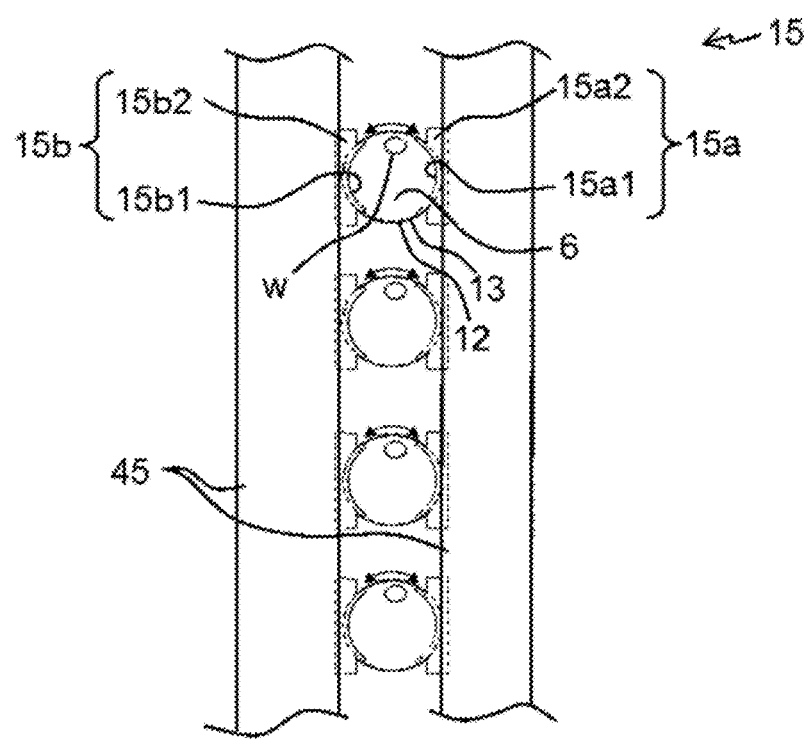
FIG. 9 is a partial enlarged plan view of a processing container 50 of the exogenous substance transfer apparatus 41 in the third embodiment.

As shown in FIG. 9, the plate-shaped strips 45a, 45b are disposed such that they respectively overlap (are in contact with) the connecting portions 15a2, 15b2 of the electrode portions 15. The electrodes 15a, 15b are thus electrically connected to the plate-shaped strips 45a, 45b, respectively. The voltage can be supplied from the power supply 9 to each of the electrodes 15a, 15b.

The processing container 50 is formed from the same sort of insulating material as the containers 12. Even though the high direct current voltage is supplied from the power supply 9, the amount of current that flows to the processing container 50 is tiny. The apparatus 41 is thus able to apply the voltage to a plurality of the containers 12 in parallel. By applying the voltage from the power supply 9 in a state in which the liquid droplets W of the cell suspension liquid have been formed in each of the containers 12, in which the oil 6 is contained, the apparatus 41 is able to perform the processing that introduces the exogenous substance in all eight of the containers 12 that are contained in one column of the containers 12 in parallel.

With the plate-shaped strip portion 45 installed on the top face of the top plate 40c such that it flanks one column of the containers 12, the apparatus 41 is configured to perform the processing in parallel for the eight containers 12 that are contained in the one column There are no particular restrictions on the number of the containers 12 to which the voltage is applied by the plate-shaped strip portion 45 and on the shape of the plate-shaped strip portion 45, as long as the apparatus 41 is able to perform the processing in parallel for a plurality of the containers 12. The plate-shaped strip portion 45 may also be configured such that it can be mounted on and removed from the processing container 50. By moving the plate-shaped strip portion 45 after the processing for one column has been completed and setting the plate-shaped strip portion 45 such that it flanks a different column, the apparatus 41 may perform the processing sequentially for one column at a time.

In the embodiments that are described above, the process that forms the liquid droplet W by putting the cell suspension liquid that contains the target cell and the exogenous substance into the oil through the opening portion in the container is equivalent to a first process. The process that moves the liquid droplet W back and forth between the electrodes by the action of the electric field that is generated by the applying of the voltage from the power supply 9 for a specified length of time is equivalent to a second process. Accordingly, in the embodiments that are described above, the cell suspension liquid is made using an animal cell as the target cell and a gene as the exogenous substance, and the liquid droplet is formed between the electrodes by putting the cell suspension liquid into the container. Thereafter, an animal cell into which a gene has been introduced (an exogenous substance-bearing cell) is manufactured by supplying the voltage from the power supply 9 to the electrodes.

An exogenous substance transfer apparatus 61 (hereinafter called the apparatus 61) in a fourth embodiment will be explained with reference to FIG. 10. The parts that are the same as in the first to the third embodiments are assigned the same reference numerals, and explanations of them will hereinafter be omitted. In the apparatus 61, a plurality of the electrode portions 35 are disposed in a single container 62. The apparatus 61 is configured such that the processing that introduces an exogenous substance can be performed in parallel for each one of the plurality of the electrode portions 35. Each one of the plurality of the electrode portions 35 includes a pair of electrodes 35a, 35b. The electrode 35b has the same shape as the electrode 35a. The electrode 35b has a planar sheet portion 35b1, which corresponds to the planar sheet portion 35a1 of the electrode 35a, and a connecting portion 35b2, which corresponds to the 35a2.

Figure 10:
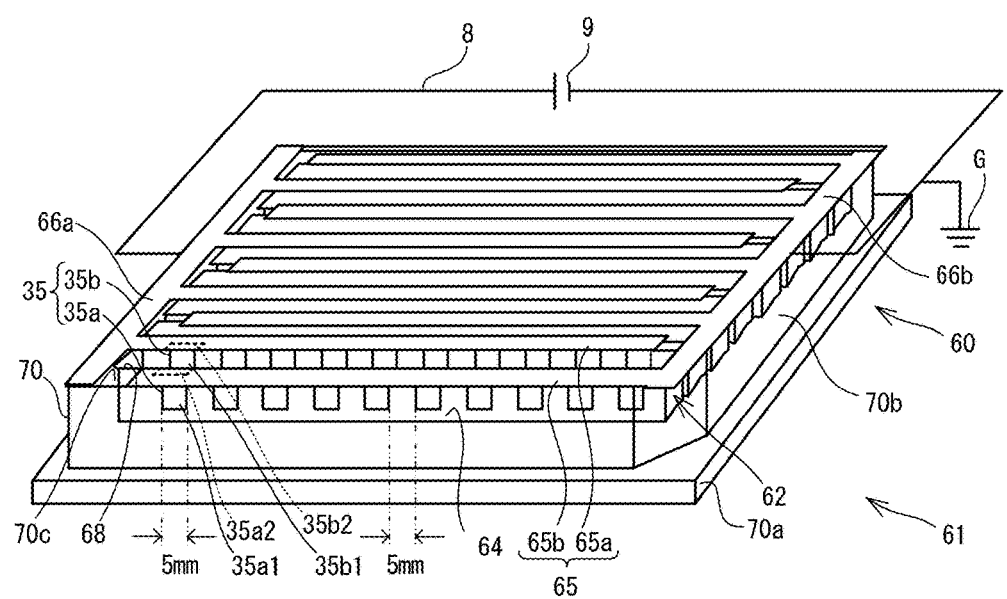
FIG. 10 is a drawing that shows an outline of an exogenous substance transfer apparatus 61 in a fourth embodiment.

As shown in FIG. 10, the apparatus 61 is provided with a processing container 60. The processing container 60 includes eight of the containers 62, which are three-dimensional rectangles whose long axes extend in the left-right direction in a plan view. The container 62 is provided with a bottom face portion 64 and an opening portion 68. The processing container 60 is provided with a support body 70, in which a rectangular frame 70a, four side wall faces 70b that extend upward from a top face of the frame 70a, and a top plate 70c that spans the top edges of the side wall faces 70b are formed into a single unit. The plurality of the containers 62 are held by the support body 70.

Rectangular through-holes of the same size as the inner periphery of the opening portions 68 of the containers 62 are formed in the top plate 70c. The top faces of side walls of the containers 62 are joined to the bottom face of the top plate 70c in positions where the through-holes in the top plate 70c are aligned to the opening portions 68 of the containers 62. The heights of the containers 62 are the same as the heights of the side wall faces 70b. The containers 62 are thus formed into a single unit with the support body 70 by being affixed to the top plate 70c in a state in which they are suspended above an installation surface of the processing container 60 by a distance that is equal to the height of the frame 70a.

The eight containers 62 are arrayed in eight rows. A plurality of the electrode portions 35 are disposed at specified intervals (for example, 5 millimeters) in each one of the containers 62. The electrodes 35a are disposed as described below. The connecting portions 35a2 are placed on the top face of the top plate 70c. The height of the sheet portions 35a1 is less than the height of side walls 63 of the containers 62. The bottom edges of the sheet portions 35a1 are positioned higher than the bottom face potions 64 of the containers 62. There is no particular restriction on the size of the sheet portion 35a1, as long as it is a size that can form an electric field that can move the liquid droplet W well within the container 62. The width of the sheet portion 35a1 may be 5 millimeters, for example. The electrodes 35b are set into the containers 62 in the same manner as the electrodes 35a, with a specified gap between the electrodes 35b and the electrodes 35a.

A plate-shaped portion 65, which includes long, narrow, rectangular plate-shaped strips 65a, 65b that extend in the lengthwise direction of the containers 62, is provided in the top plate 70c. The plate-shaped portion 65 is formed from an electrically conductive material such as a metal or the like. The lengths of the plate-shaped strips 65a, 65b in the lengthwise direction are substantially the same dimension as the length of the top plate 70c in the lengthwise direction (the lengthwise direction of the containers 62). The lengths of the plate-shaped strips 65a, 65b in the shorter direction are substantially the same as the gap between adjacent rows of the containers 62. Long, narrow, rectangular plate-shaped strips 66a, 66b are placed along the left and right edges, respectively, of the top plate 70c, extending in the shorter direction of the plate-shaped strips 65a, 65b. The plate-shaped strips 65a, 65b are each connected to the plate-shaped strips 66a, 66b. As a whole, the plate-shaped portion 65 and the plate-shaped strips 66a, 66b have the shape of a pair of intermeshed combs. More specifically, the plate-shaped strips 65a, which are even-numbered when counted from the bottom side of FIG. 10, are connected to the plate-shaped strip 66a that is placed along the left edge of the top plate 70c. The plate-shaped strips 65b, which are odd-numbered when counted from the bottom side of FIG. 10, and the plate-shaped strip 66a are separated from one another. The plate-shaped strips 65b are connected to the plate-shaped strip 66b that is placed along the right edge of the top plate 70c. The plate-shaped strips 65a and the plate-shaped strip 66b are separated from one another. Electrical contact points with the conductor 8 are provided in the plate-shaped strips 66a, 66b. The plate-shaped strip 66a is connected to the positive electrode of the power supply 9 through the conductor 8, which is connected to the electrical contact point. The plate-shaped strip 66b is connected to the negative electrode of the power supply 9 through the conductor 8, which is connected to the electrical contact point.

The plate-shaped strips 65a, 65b are disposed such that they respectively overlap (are in contact with) the connecting portions 35a2, 35b2 of the electrode portions 35. The electrodes 35a, 35b are thus electrically connected to the plate-shaped strips 65a, 65b, respectively. The voltage can be supplied from the power supply 9 to each of the electrodes 35a, 35b.

The processing container 60 and the containers 62 are formed from insulating material. Even though the high direct current voltage is supplied from the power supply 9, the amount of current that flows to the processing container 60 is tiny. Therefore, in the apparatus 61, the voltage can be supplied to a plurality of the pairs of the electrodes in parallel. By applying the voltage from the power supply 9 in a state in which the liquid droplets W of the cell suspension liquid have been formed each of the containers 62, in which the oil 6 is contained, the apparatus 61 is able to perform the processing that introduces the exogenous substance in all of the liquid droplets that are disposed between the plurality of electrode pairs in the processing container 60.

In the apparatus 61, the shape and the number of the containers 62 with which the processing container 60 is provided may be varied as desired. The number of the electrodes that are disposed in any one of the containers 62, and the shape of electrodes, may be varied as desired. More specifically, the apparatus 61 may be provided with any electrode portions by which an electric field is formed in which the distribution of the lines of electric force is non-uniform, such as a plurality of the electrode portions 15, for example (refer to FIG. 3). In the same manner as in the third embodiment, the apparatus 61 may be provided with a plurality of pairs of electrodes that are configured such that they can be mounted in and removed from the processing container 60, and by moving the plurality of the electrodes after the processing for one of the containers 62 has been completed and setting the plurality of the electrodes in a different one of the containers 62, the apparatus 61 may perform the processing sequentially for one of the containers 62 at a time.

The present invention has been explained above, based on the various embodiments, but the present invention is not limited to the embodiments that are described above, and it can easily be inferred that various types of improvements can be made within the scope of the present invention. For example, the surface portions of the various electrodes (the electrodes, 5a, 5b, 15a, 15b, 25a, 25b, 35a, 35b) that are mentioned in the embodiments that are described above are formed as smooth surfaces, but they are not limited to being smooth surfaces. In the exogenous substance transfer apparatus, one of the surface portions of the electrode portions 5, 25 and the sheet portions of the electrodes 15, 35 may be provided as at least one of a recessed portion and a raised portion, for example, and the non-uniform electric field may be formed between the electrodes by the at least one of the recessed portion and the raised portion. The individual electrodes do not necessarily have to extend in a direction that is orthogonal to the horizontal plane, and they may also be provided such that they intersect the horizontal plane. In a case where a disposable container or a general-purpose container is used, for example, it is acceptable for the containers not to be provided in any one of the exogenous substance transfer apparatuses 1, 11, 41, and 61. In that case, the exogenous substance transfer apparatus demonstrates the same sort of effects as the apparatuses 1, 11, 41, and 61 by using pairs of electrodes that are disposed within the containers such that they are separated from one another.

Figure 11:
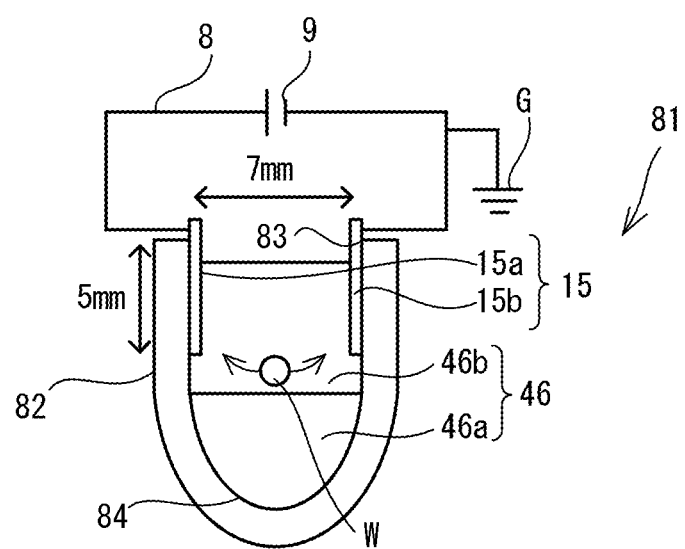
FIG. 11 is a drawing that shows an outline of an exogenous substance transfer apparatus 81 in a modified example.

Two types of insulating liquids with different specific gravities may be used as the insulating liquid. In the modified example, the processing is performed by an exogenous substance transfer apparatus 81 (hereinafter called the apparatus 81), an example of which is shown in FIG. 11, for example. The parts that are the same as in the first to the fourth embodiments are assigned the same reference numerals, and explanations of them will hereinafter be omitted. The apparatus 81 in the modified example is provided with a container 82, the electrode portion 15, the conductor 8, and the power supply 9. The container 82 is a cylindrical container that has a bottom, and it includes a hemispherical bottom face portion 84 and an opening portion 83 with a diameter of 7 millimeters. The container 82 is formed from an insulating material. The container 82 is configured to contain an insulating liquid 46. The insulating liquid 46 includes a first insulating liquid 46a and a second insulating liquid 46b. The specific gravity of the second insulating liquid 46b is lighter than the specific gravity of the first insulating liquid 46a. The first insulating liquid 46a may be a fluorocarbon oil (with a specific gravity that is greater than 1), for example. The second insulating liquid 46b may be a silicone oil (with a specific gravity from 0.9 to 1) that has a kinematic viscosity of 30 cSt, for example. The electrode portion 15 includes the pair of the electrodes 15a, 15b. The pair of the electrodes 15a, 15b are in contact with the second insulating liquid 46b, but are not in contact with the first insulating liquid 46a. The distance from the opening portion 83 to the bottom edges of the electrodes 15a, 15b is 5 millimeters.

Figure 12:
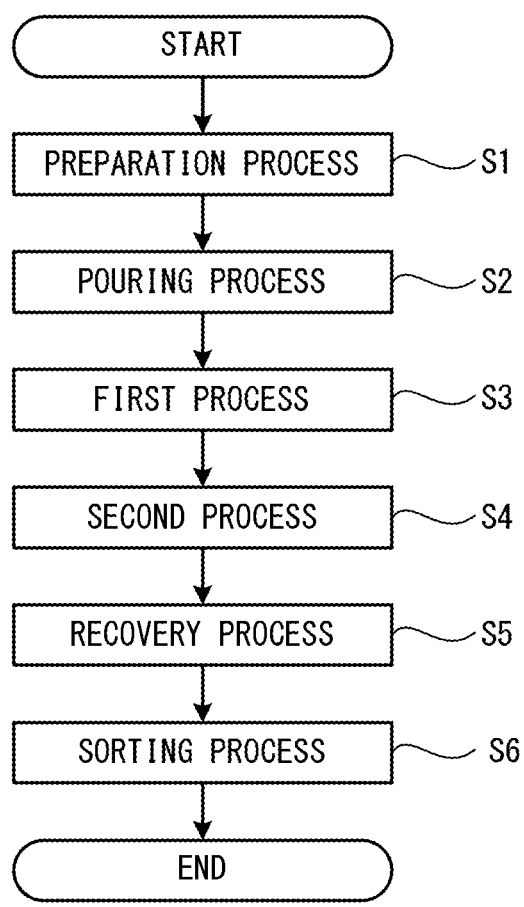
FIG. 12 is a flowchart of a process for manufacturing an exogenous substance-bearing cell in the modified example.

In the modified example, the processing is performed by the processing that is shown in FIG. 12, for example. As shown in FIG. 12, a cell suspension liquid that contains cells and a exogenous substance is adjusted (Step S1). Prior to a first process, the first insulating liquid 46a and the second insulating liquid 46b are poured into the container 82 (Step S2). At Step S2, a layer of the second insulating liquid 46b is formed on top of a layer of the first insulating liquid 46a, due to the difference in their specific gravities. The cell suspension liquid that was adjusted at Step S1 is supplied to the container 82 into which the first insulating liquid 46a and the second insulating liquid 46b were supplied at Step S2 (Step S3). The liquid droplet W of the cell suspension liquid is formed within the layer of the second insulating liquid 46b by Step S3. The direct current voltage is applied from the power supply 9 to the pair of the electrodes 15a, 15b for a specified length of time (Step S4). At Step S4, the liquid droplet W moves back and forth within the second insulating liquid 46b between the pair of the electrodes 15a, 15b, due to the action of the electric field that is generated between the pair of the electrodes 15a, 15b. In the region above the boundary between the layer of the first insulating liquid 46a and the layer of the second insulating liquid 46b (on the side toward the surface of the second insulating liquid 46b), the liquid droplet W moves along parabolic lines that curve upward from the boundary, as shown in FIG. 11. After the application of the voltage has been terminated, the liquid droplet W is recovered from the insulating liquid 46 (the second insulating liquid 46b) (Step S5). The exogenous substance-bearing cells are obtained by sorting out, from among the cells in the recovered liquid droplet, the cells into which the exogenous substance has been introduced (Step S6).

The method for manufacturing the exogenous substance-bearing cells in the modified example is able to move the liquid droplet W smoothly within the second insulating liquid 46b. The present manufacturing method is able to introduce the exogenous substance into the cells with a better transfection efficiency than would be the case if the liquid droplet did not move smoothly. The method for manufacturing the exogenous substance-bearing cells in the modified example may be used in any one of the apparatus 1, the apparatus 11, the apparatus 41, and the apparatus 61. The order of the process at Step S1 and the process at Step S2 may be switched. In a case where the processing is performed repeatedly using the same apparatus, the processing at Step S2 may be omitted after the first round.

Example 1

Hereinafter, the present invention will be explained in greater detail using examples. The present invention is not limited to the examples below. The materials that are used in the examples are described below.

Silicone oil: Shin-Etsu silicone oil KF-96L-100, Shin-Etsu Chemical Co., Ltd.

PBS buffer solution: D-PBS, 0.1 mol/l phosphate-buffered saline, Wako

HEK 293 cells: Human embryonic kidney 293 (HEK 293) cell line, JCRB9068, JCRB Cell Bank Mouse Neuro-2a neuroblastoma cell line: IFO50081, JCRB Cell Bank Elderly (age 81) human dermal fibroblast cell line: JCRB0532 TIG-107, JCRB Cell Bank First-generation mouse hippocampal nerve cells: MB-X0403, Sumitomo Bakelite Co., Ltd.

Plasmid DNA 1: Venus, plasmid DNA encoding yellow (yellow-green) fluorescent protein, RIKEN Plasmid DNA 2: EGFP, plasmid DNA encoding green fluorescent protein, Clontech Laboratories, Inc.

Plasmid DNA 3: mCherry, plasmid DNA encoding red fluorescent protein, Clontech Laboratories, Inc.

Trypan blue: Trypan blue, 0.4% solution, MP Biomedicals, LLC.

Retinoic acid: All-trans Retinoic Acid, Wako.

Evaluations of the effects of introducing exogenous genes were conducted by the methods hereinafter described.

Evaluation of gene transfection efficiency The plasmid DNA 1 was selected as an exogenous gene, and the liquid droplet in the oil was recovered by a micropipette after the gene transfer operation. The recovered liquid droplet was moved to a liquid culture medium, then incubated overnight under conditions of 37° C. and 5% carbon dioxide. The total number of cells in a bright field observation was measured using a fluorescent microscope (Nikon TE2000U), and in a fluorescent observation, the number of cells that emitted fluorescent light (cells into which the exogenous gene had been introduced) was counted. The gene transfection efficiency was computed by dividing the number of fluorescing cells by the total number of cells.

Evaluation of Survival Rate

The pigment trypan blue, which specifically stains dead cells, was used for measuring the survival rate of the target cells. The liquid droplet in the oil was recovered by a micropipette after the gene transfer operation (that is, after the application of the voltage for the specified length of time) and suspended in the PBS buffer solution. The cells in the liquid droplet were then stained with the trypan blue and observed in a bright field using one of a Countess Automated Cell Counter (Life Technologies) and a microscope (Nikon TE2000U). The number of live cells (the number of unstained cells) and the number of dead cells (the number of stained cells) were counted separately, and the survival rate was computed by dividing the number of live cells by the total number of cells (the sum of the number of live cells and the number of dead cells).

First Example

The apparatus 1 that is shown in FIG. 1 was created by the procedure that is hereinafter described. A disposable polystyrene spectrophotometer cell (a macro cuvette, 759007, PEQLAB) with a width of 10 millimeters was used as the container. Aluminum tapes (Furuto Industrial Co., Ltd.) that serve as the electrodes were affixed to the entire surfaces of a pair of inner walls of the container that face one another. An opening portion in the top face of the container is clamped by electrically conductive clips, and the aluminum tapes and the clips are in contact. The clips and a high-voltage direct current power supply (HAR-30R10, Matsusada Precision, Inc.) are connected by a conductor wire, such that the high-voltage direct current power supply and the aluminum tapes are electrically connected. A silicone oil with a kinematic viscosity of 100 cSt is poured into the container up to a seventh demarcation and is left to stand. Ultrapure water that is manufactured using an ultrapure water manufacturing unit (Milli-Q, Millipore Corporation) is dripped into the container in 3-microliter droplets by a pipette, such that spherical liquid droplets with a diameter of approximately 1.8 millimeters are formed in the silicone oil. Next, a voltage of 3.5 kV (electric field intensity of 3.5 kV/cm) is applied by the high-voltage direct current power supply. The movements of the liquid droplets are photographed by a high-speed camera (FASTCAM-1280PCI, Photron), and the number of cycles of back-and-forth movement of the liquid droplets are counted by visual observation while the photographed motion picture is replayed as low speed. The results confirmed that the liquid droplets moved back and forth between the aluminum tapes approximately 100 times in a 1-minute interval and that the liquid droplets came into contact with the aluminum tapes. The examples that are hereinafter described were carried out using the same sort of aluminum tapes and the same sort of high-voltage direct current power supply as in the first example.

Second Example

The apparatus 41 that is shown in FIG. 8 is created by the procedure that is hereinafter described. A 96-hole cell culturing plate (Cat. No. 92696, TPP) that has 96 cylindrical containers (wells) that have bottoms and inside diameters of 6.7 millimeters is used as the processing container. Two aluminum tapes (electrodes) with widths of 5 millimeters are affixed to the inner circumferential faces of each of four adjacent containers among the eight containers that reside in a single column in the processing container, such that the aluminum tapes face one another. The two aluminum tapes are disposed with gaps formed between them, such that neither one of the two aluminum tapes is in contact with the other at their respective edges in the circumferential direction. The distance between the electrodes is 6 millimeters at the narrowest point (between the edges of the aluminum tapes). Each one of the aluminum tapes is extended to the outside of the container at the top of the container and affixed to the top plate of the processing container, which is formed between the columns of the containers. In the top plate, rectangular pieces of metal foil are disposed such that they flank the containers and extend along the direction of the columns of the containers. Each of the pieces of metal foil is in contact with the top faces (connecting portions) of the aluminum tapes that have been extended to the outside of the containers. One end of each of the pieces of metal foil is electrically connected to the positive electrode of the high-voltage power supply. The other end of each of the pieces of metal foil is electrically connected to the negative electrode of the high-voltage power supply. The voltage can thus be applied to each one of the containers.

A silicone oil with a kinematic viscosity of 100 cSt is poured into each of the four containers and is left to stand. Ultrapure water that is manufactured using the ultrapure water manufacturing unit (Milli-Q, Millipore Corporation) is dripped into each of the containers in 3-microliter droplets by a pipette, such that spherical liquid droplets with a diameter of approximately 1.8 millimeters are formed in the silicone oil. A voltage of 1 kV (electric field intensity of 1.67 kV/cm) is applied by the high-voltage direct current power supply. In each of the four containers, it was confirmed that the liquid droplets moved back and forth between the aluminum tapes approximately 300 times in 1 minute at the points where the distance between the electrodes in the container was the shortest. The confirmation of the movements of the liquid droplets was carried out by the same sort of technique as in the first example. The fact that the number of back-and-forth movements of the liquid droplets was greater in the second example than in the first example is thought to be due to locally greater electric field strengths close to the edges of the electrodes.

Third Example

A test to introduce an exogenous gene into the human embryonic kidney HEK 293 cell line was carried out using the apparatus 41 that was created in the second example. A culture medium (hereinafter called the prepared culture medium) was prepared that contains Dulbecco's Modified Eagle's Medium High Glucose (DMEM, Wako), 10% fetal bovine serum (FBS), and penicillin-streptomycin (Wako). The prepared culture medium was poured into a plastic Petri dish (Orange Scientific; hereinafter simply called the Petri dish) with a diameter of 10 centimeters. The human embryonic kidney (HEK) 293 cell line was added to the Petri dish to a concentration of $1.0 \times 10^6$ cells per milliliter and were incubated under conditions of 37° C. and 5% carbon dioxide. The human embryonic kidney HEK 293 cell line that was extracted from the Petri dish by 0.05% trypsin—0.53 mmol/IEDTA-4Na (Wako) were suspended in the PBS buffer solution. The concentration of the human embryonic kidney HEK 293 cell line in the PBS buffer solution was prepared to $1.0 \times 10^4$ cells per droplet (that is, $1.0 \times 10^4$ cells in a 3-microliter liquid droplet). The cell suspension liquid was then prepared by adding the plasmid DNA 1 to the PBS buffer solution at a concentration of 258 nanograms per microliter. The prepared cell suspension liquid was dripped in 3-microliter droplets into the containers, which contained silicone oil with a kinematic viscosity of 100 cSt as the insulating oil, such that spherical liquid droplets with a diameter of approximately 1.8 millimeters were formed.

Voltages of 1.0 to 4 kV were applied from the high-voltage direct current power supply to the containers in which the liquid droplets were formed for zero to 15 minutes (0.5 minutes, 1 minute, 2 minutes, 3 minutes, 4 minutes, 5 minutes, 15 minutes). Tests with a voltage application time of 30 minutes were also conducted in order to measure the survival rates. The test results as shown in FIGS. 13 and 14.

Figure 13:
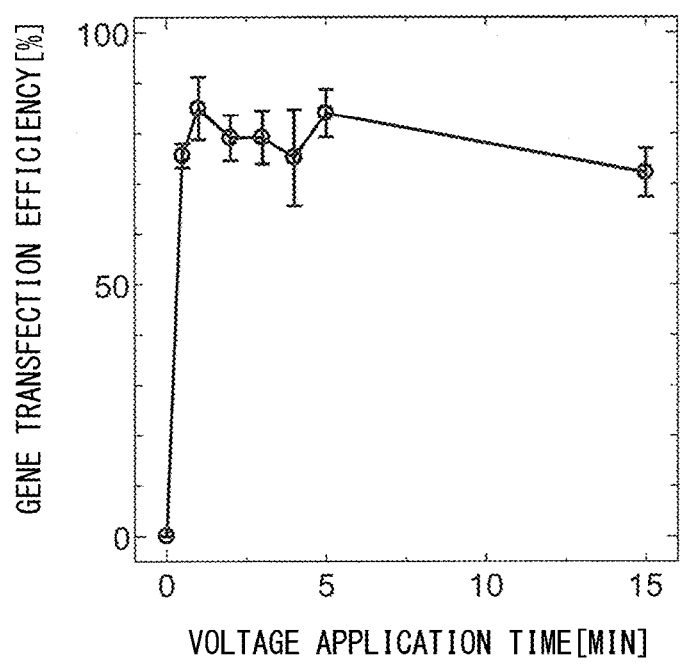
FIG. 13 is a graph that shows results of an evaluation of gene transfer efficiency one day after an operation to introduce an exogenous gene into the human embryonic kidney 293 (HEK 293) cell line in a third example.
Figure 14:
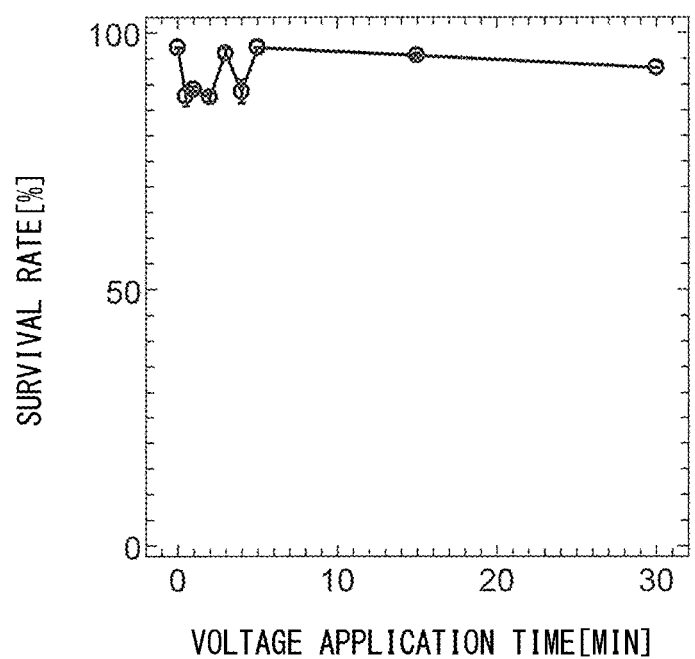
FIG. 14 is a graph that shows results of an evaluation of survival rates immediately after the operation to introduce the exogenous gene into the human embryonic kidney 293 (HEK 293) cell line in the third example.

The horizontal axis in FIG. 13 shows the voltage application time, and the vertical axis shows the gene transfection efficiency. The gene transfection efficiency in relation to the voltage application time is shown by a solid line. As shown in FIG. 13, a gene transfection efficiency of 70% to 90% is achieved at all of the voltage application times except zero minutes, indicating that the method in the third example is a method that is not inferior to the known techniques. The horizontal axis in FIG. 14 is the voltage application time, and the vertical axis is the survival rate for the target cells. The survival rate in relation to the voltage application time is shown by a solid line. As shown in FIG. 14, the survival rate did not fall below 80%, even in the case where the voltage application time reached 30 minutes. The results described above indicate that both a high gene transfection efficiency and a high survival rate are achieved by using the apparatus 41 to introduce an exogenous gene into the target cells.

Figure 15:
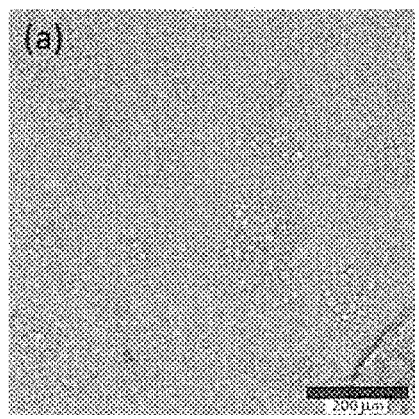
FIG. 15 is a microscopic observation image (magnification 10×) of the human embryonic kidney 293 (HEK 293) cell line in a bright field, observed one day after an operation to introduce a plasmid DNA 1 gene by applying a direct current voltage for five minutes in the third example.
Figure 16:
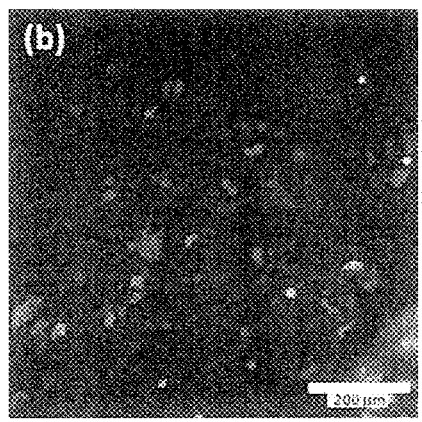
FIG. 16 is a fluorescence image (magnification 10×) of the human embryonic kidney 293 (HEK 293) cell line, observed one day after the operation to introduce the plasmid DNA 1 gene by applying the direct current voltage for five minutes in the third example.
Figure 17:
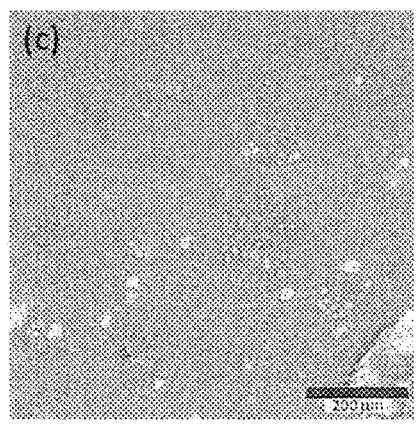
FIG. 17 is a merged image (magnification 10×) of the bright-field image and the fluorescent-field fluorescence image of the human embryonic kidney 293 (HEK 293) cell line, observed one day after the operation to introduce the plasmid DNA 1 gene by applying the direct current voltage for five minutes in the third example.

A bright field image that is shown in FIG. 15 is an image that was observed under white transmitted light. A fluorescence image that is shown in FIG. 16 is an image that was observed in a dark field, with a mercury lamp light source serving as the light source, the target cells being illuminated through a filter by excitation light with a wavelength close to 490 nanometers, and fluorescent light with a wavelength close to 510 nanometers being observed through a filter. A merged image that is shown in FIG. 17 is an image in which the bright-field image and the fluorescence image have been combined by image processing. Based on the fluorescence image that is shown in FIG. 16, it was confirmed that the fluorescent protein that is encoded by the plasmid DNA 1 was expressed within the target cells (white and gray areas), indicating that the transfection of the gene was successful.

Fourth Example

The mouse Neuro-2a neuroblastoma cell line was added to a Petri dish, into which the prepared culture medium had been poured, to a concentration of $1.0 \times 10^6$ cells per milliliter and were incubated under conditions of 37° C. and 5% carbon dioxide. Then the retinoic acid was also added, to a final concentration of 5 micromoles per liter, the mouse Neuro-2a neuroblastoma cell line was differentiated into nerve-like cells by being incubated overnight under conditions of 37° C. and 5% carbon dioxide. The cell suspension liquid was prepared by adding the differentiated mouse Neuro-2a neuroblastoma cell line to the PBS buffer solution to a concentration of $1.0 \times 10^5$ cells per droplet (that is, $1.0 \times 10^5$ cells in a 3-microliter liquid droplet), and by adding the plasmid DNA 1 that was created in the second example was used. The liquid droplets were formed in the silicone oil by dripping the cell suspension liquid in 3-microliter droplets into the containers, which contained silicone oil with a kinematic viscosity of 100 cSt. A voltage of 3.8 kV was then applied to the pairs of the electrodes for five minutes. After the voltage was applied, the liquid droplets that were recovered from the oil were added to a glass bottom plate (EZView Glass Bottom Culture Plate, Iwaki) with six wells, into which the prepared culture medium had been poured, and incubated under conditions of 37° C. and 5% carbon dioxide. The cells were observed by microscope one day and three days after the start of the culturing. With a mercury lamp light source serving as the light source, the target cells were illuminated through a filter by excitation light with a wavelength close to 490 nanometers, and fluorescent light with a wavelength close to 510 nanometers was observed through a filter. The test results are shown in FIGS. 18 to 20.

Figure 18:
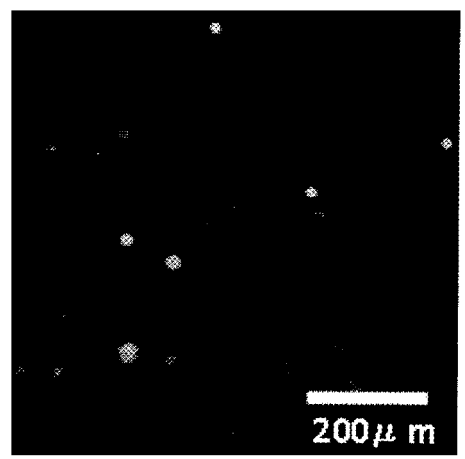
FIG. 18 is a fluorescence image (magnification 10×) of the mouse Neuro-2a neuroblastoma cell line, observed one day after a gene transfer operation in a fourth example.
Figure 19:
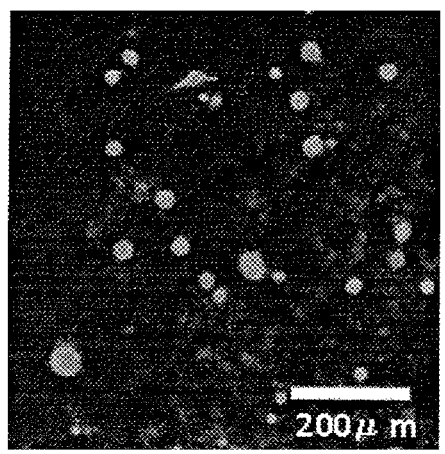
FIG. 19 is a fluorescence image (magnification 10×) of the mouse Neuro-2a neuroblastoma cell line, observed three days after a gene transfer operation in the fourth example.
Figure 20:
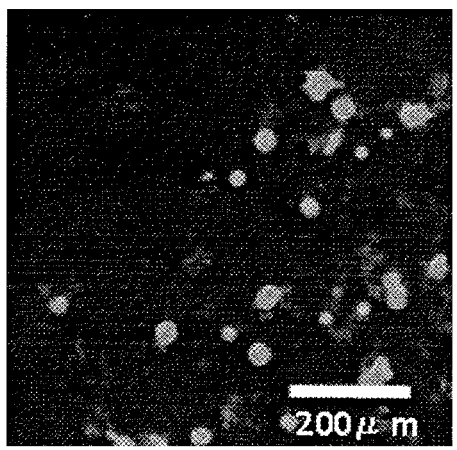
FIG. 20 is a fluorescence image (magnification 10×) of the mouse Neuro-2a neuroblastoma cell line, observed three days after the gene transfer operation in the fourth example.
Figure 21:
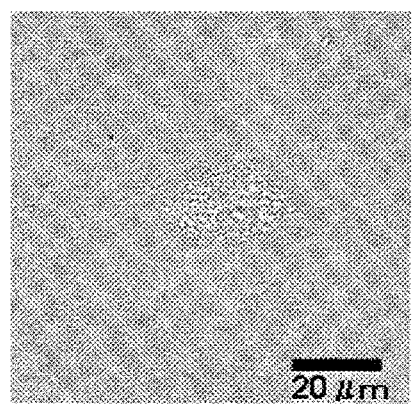
FIG. 21 is a microscopic observation image (magnification 60×) of an elderly human dermal fibroblast cell line in a bright field, observed three days after an operation to introduce a gene in the fifth example.

As shown in FIGS. 18 to 20, it was confirmed by fluorescence (white and gray areas) that the exogenous gene (the plasmid DNA 1) had been introduced well into the differentiated nerve-like cells, into which the transfection of an exogenous gene tends to be difficult.

Fifth Example

The elderly (age 81) human dermal fibroblast cell line was added to a Petri dish, into which the DMEM (Wako) had been poured, to a concentration of $1.0 \times 10^6$ cells per milliliter and were incubated under conditions of 37° C. and 5% carbon dioxide. Then the cell suspension liquid was prepared by adding the elderly (age 81) human dermal fibroblast cell line to the PBS buffer solution to a concentration of $1.0 \times 10^4$ cells per droplet (that is, $1.0 \times 10^4$ cells in a 3-microliter liquid droplet), and by adding the plasmid DNA 1 at a concentration of 260 nanograms per microliter. The apparatus 41 that was created in the second example was used. The prepared cell suspension liquid was dripped in 3-microliter droplets into the containers, which contained silicone oil with a kinematic viscosity of 100 cSt, and a voltage of 3.8 kV was applied for 5 to 30 minutes. After the voltage was applied, the liquid droplets that were recovered from the oil were added to a glass bottom plate with six wells, into which the prepared culture medium had been poured, and incubated under conditions of 37° C. and 5% carbon dioxide. The cells were observed by microscope three days after the start of the culturing. With a mercury lamp light source serving as the light source, the target cells were illuminated through a filter by excitation light with a wavelength close to 490 nanometers, and fluorescent light with a wavelength close to 510 nanometers was observed through a filter. The test results are shown in FIGS. 21 to 29.

Figure 22:
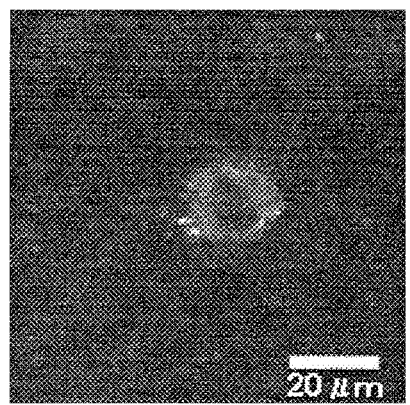
FIG. 22 is a fluorescence image (magnification 60×) of the elderly human dermal fibroblast cell line, observed three days after the operation to introduce the gene in the fifth example.
Figure 23:
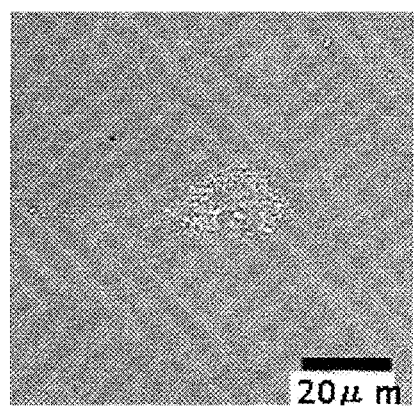
FIG. 23 is a merged image (magnification 60×) of the bright-field image and the fluorescent-field fluorescence image of the elderly human dermal fibroblast cell line, observed three days after the operation to introduce the gene in the fifth example.
Figure 24:
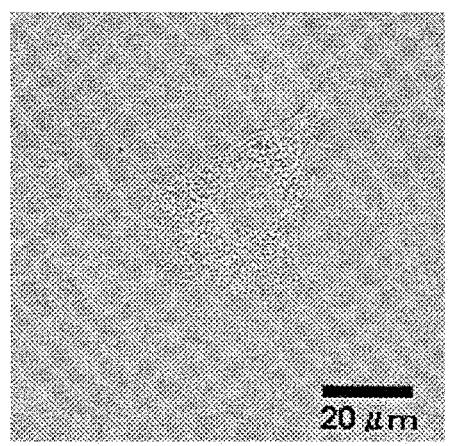
FIG. 24 is a microscopic observation image (magnification 60×) of an elderly human dermal fibroblast cell line in a bright field, observed three days after an operation to introduce a gene in a fifth example.
Figure 25:
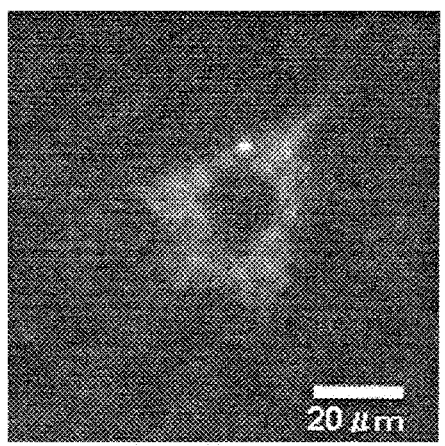
FIG. 25 is a fluorescence image (magnification 60×) of the elderly human dermal fibroblast cell line, observed three days after the operation to introduce the gene in the fifth example.
Figure 26:
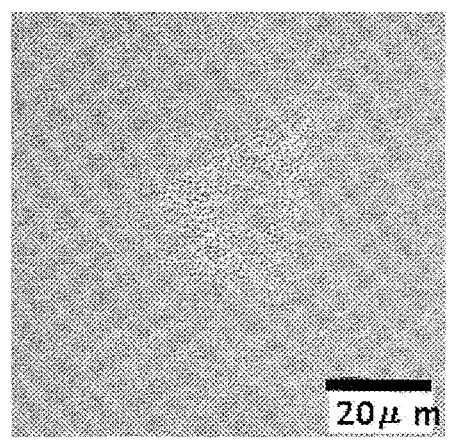
FIG. 26 is a merged image (magnification 60×) of the bright-field image and the fluorescent-field fluorescence image of the elderly human dermal fibroblast cell line, observed three days after the operation to introduce the gene in the fifth example.
Figure 27:
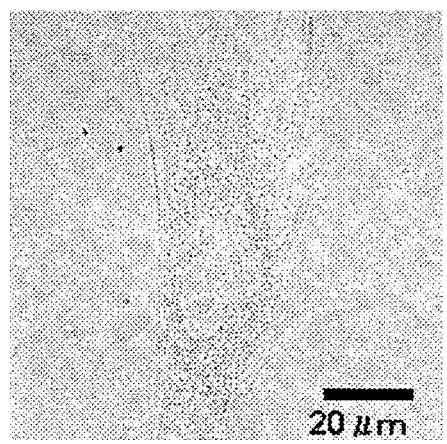
FIG. 27 is a microscopic observation image (magnification 60×) of an elderly human dermal fibroblast cell line in a bright field, observed three days after an operation to introduce a gene in the fifth example.
Figure 28:
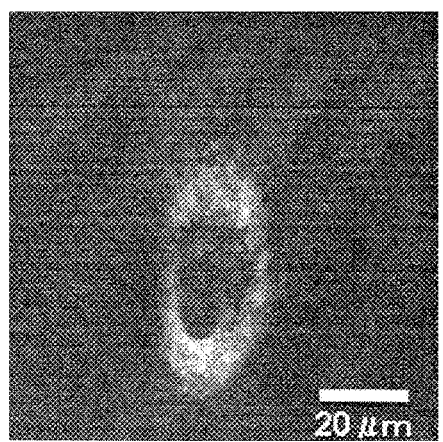
FIG. 28 is a fluorescence image (magnification 60×) of the elderly human dermal fibroblast cell line, observed three days after the operation to introduce the gene in the fifth example.
Figure 29:
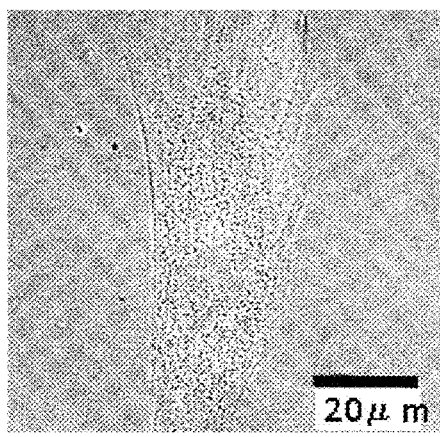
FIG. 29 is a merged image (magnification 60×) of the bright-field image and the fluorescent-field fluorescence image of the elderly human dermal fibroblast cell line, observed three days after the operation to introduce the gene in the fifth example.

As shown in FIGS. 22, 25, and 28, it was confirmed by fluorescence (white and gray areas) that the exogenous gene (the plasmid DNA 1) had been introduced into the elderly (age 81) human dermal fibroblast cell line. Thus, according to the method for manufacturing the exogenous substance-bearing cells in the fifth example, which uses the apparatus 41, it has been shown that an exogenous gene (an exogenous substance) is introduced well, even if the number of cells is a small amount such as $1.0 \times 10^4$ cells per droplet. In other words, it has been shown that transformation is achieved in a rare sample with superior efficiency. While fluorescence was observed in the cytoplasm of the target cell in the fluorescence images in FIGS. 25 and 28, fluorescence was observed in the nucleus (the roughly circular area) in the center of the target cell in the fluorescence image in FIG. 22. This shows that, according to the method for manufacturing the exogenous substance-bearing cells in the fifth example, an exogenous gene (an exogenous substance) is introduced well, not only into the cytoplasm of the target cell, but also into the nucleus. Thus, according to the method for manufacturing the exogenous substance-bearing cells in the fifth example, the transfection efficiency for an exogenous gene into the cell nucleus can be made better than with the known methods.

Sixth Example

Figure 30:
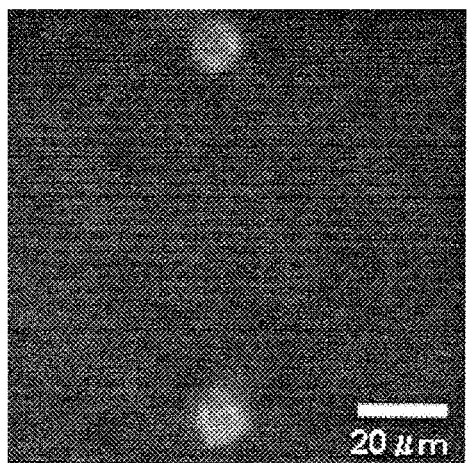
FIG. 30 is a green fluorescent-field fluorescence image (magnification 60×) of the mouse Neuro-2a neuroblastoma cell line, observed two days after a gene transfer operation in a sixth example.
Figure 31:
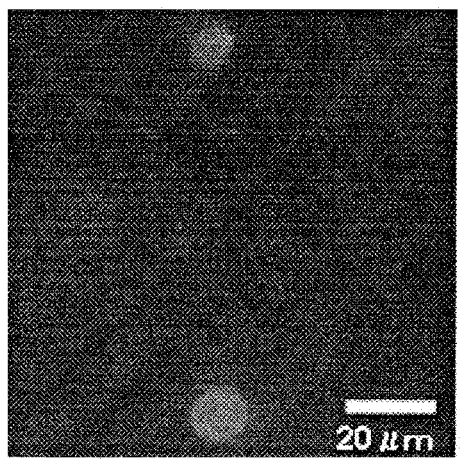
FIG. 31 is a red fluorescent-field fluorescence image (magnification 60×) of the mouse Neuro-2a neuroblastoma cell line, observed two days after the gene transfer operation in the sixth example.
Figure 32:
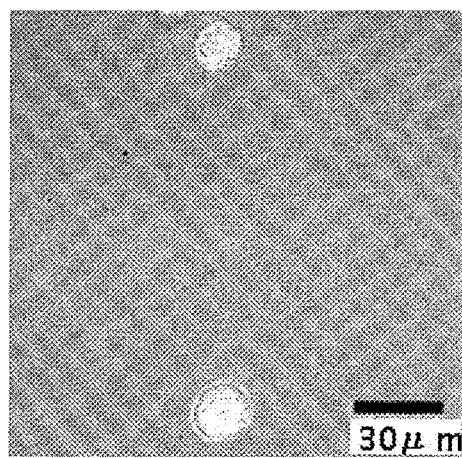
FIG. 32 is a merged image (magnification 60×) of a bright-field image, the green fluorescent-field fluorescence image, and the red fluorescent-field fluorescence image of the mouse Neuro-2a neuroblastoma cell line, observed two days after the gene transfer operation in the sixth example.
Figure 33:
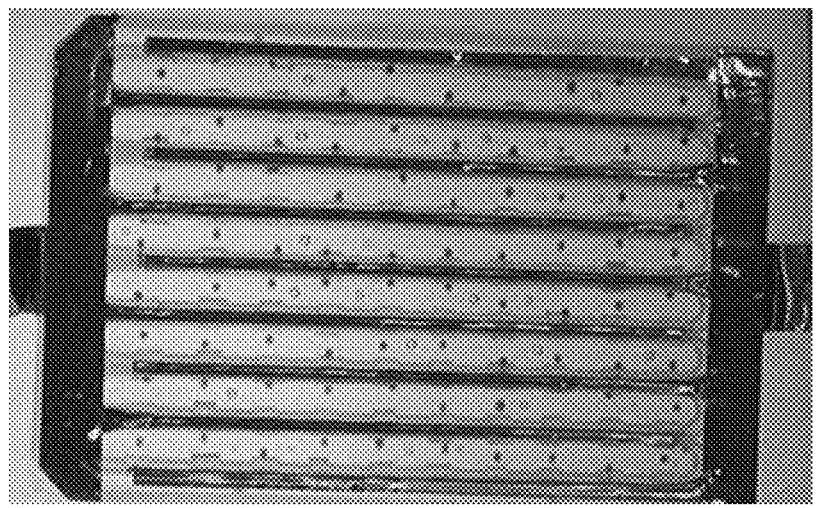
FIG. 33 is an image in a series of images taken over time that show movements of liquid droplets when a direct current voltage is applied using an apparatus of a seventh example (at reference time).
Figure 34:
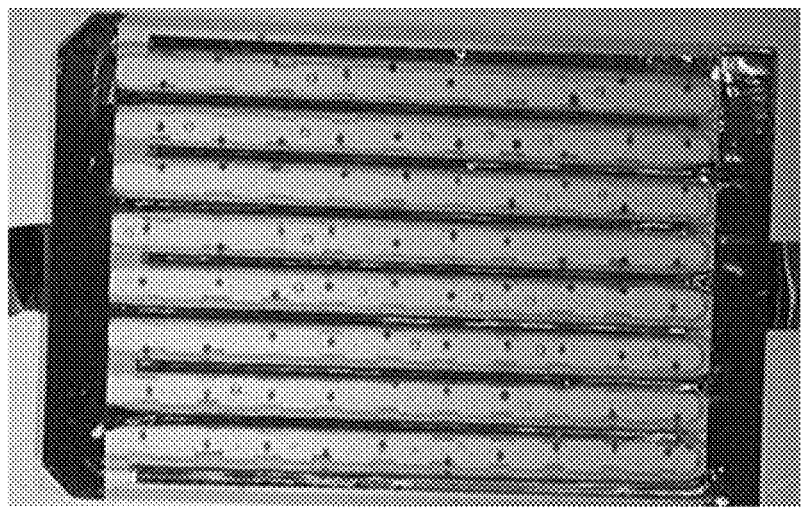
FIG. 34 is an image in the series of images taken over time that show movements of liquid droplets when the direct current voltage is applied using the apparatus of the seventh example (0.1 sec. after reference time).
Figure 35:
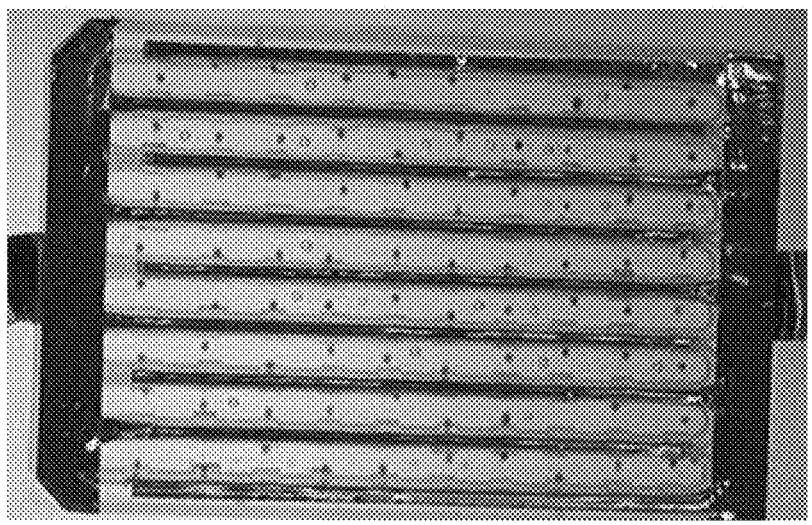
FIG. 35 is an image in the series of images taken over time that show movements of liquid droplets when the direct current voltage is applied using the apparatus of the seventh example (0.2 sec. after reference time).
Figure 36:
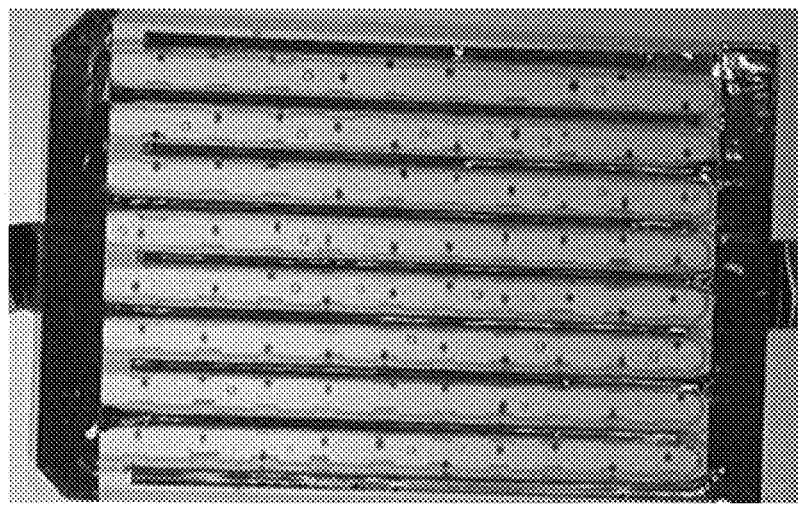
FIG. 36 is an image in the series of images taken over time that show movements of liquid droplets when the direct current voltage is applied using the apparatus of the seventh example (0.3 sec. after reference time).
Figure 37:
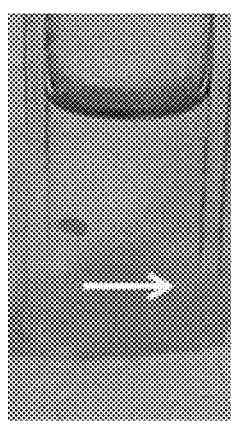
FIG. 37 is an image in a series of images taken over time that show movements of liquid droplets when a direct current voltage is applied using an apparatus of an eighth example (at reference time).
Figure 38:
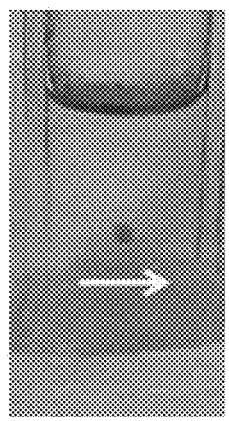
FIG. 38 is an image in the series of images taken over time that show movements of liquid droplets when the direct current voltage is applied using the apparatus of the eighth example (0.1 sec. after reference time).
Figure 39:
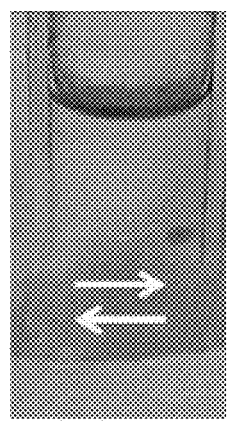
FIG. 39 is an image in the series of images taken over time that show movements of liquid droplets when the direct current voltage is applied using the apparatus of the eighth example (0.2 sec. after reference time).
Figure 40:
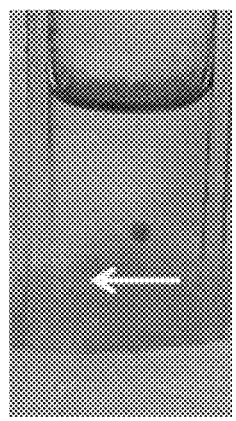
FIG. 40 is an image in the series of images taken over time that show movements of liquid droplets when the direct current voltage is applied using the apparatus of the eighth example (0.3 sec. after reference time).
Figure 41:
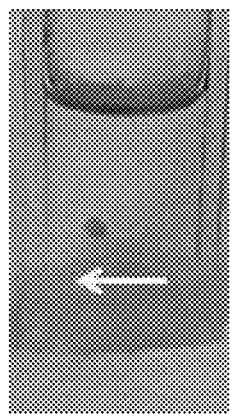
FIG. 41 is an image in the series of images taken over time that show movements of liquid droplets when the direct current voltage is applied using the apparatus of the eighth example (0.4 sec. after reference time).

The mouse Neuro-2a neuroblastoma cell line was added to a Petri dish, into which the DMEM (Wako) had been poured, to a concentration of $1.0\times10^6$ cells per milliliter and were incubated under conditions of 37° C. and 5% carbon dioxide. Then the retinoic acid was also added, to a final concentration of 5 micromoles per liter, and the cells were incubated overnight under conditions of 37° C. and 5% carbon dioxide. The cell suspension liquid was prepared by adding mouse Neuro-2a neuroblastoma cell line that had differentiated into nerve-like cells to the PBS buffer solution to a concentration of $1.0\times10^4$ cells per droplet (that is, $1.0\times10^4$ cells in a 3-microliter liquid droplet), and by adding two types of the plasmid DNA at the concentrations hereinafter described. Specifically, the plasmid DNA 2, which encodes the green fluorescent protein, was added at a concentration of 200 nanograms per microliter. The plasmid DNA 3, which encodes the red fluorescent protein, was added at a concentration of 600 nanograms per microliter. The apparatus 41 (refer to FIG. 8) that was created in the second example was used. The liquid droplets were formed by dripping the cell suspension liquid in 3-microliter droplets into the containers, which contained silicone oil with a kinematic viscosity of 100 cSt. A voltage of 3.8 kV was applied to the pairs of the electrodes for five minutes. After the voltage was applied, the liquid droplets that were recovered from the oil were added to a glass bottom plate with six wells, into which the prepared culture medium had been poured, and incubated under conditions of 37° C. and 5% carbon dioxide. The cells were observed by microscope (Olympus IX81) two days after the start of the culturing. With a mercury lamp light source serving as the light source, the target cells were illuminated through a filter by excitation light with a wavelength close to 490 nanometers, and a green fluorescent light signal with a wavelength close to 510 nanometers was observed through a filter. With a mercury lamp light source serving as the light source, the target cells were illuminated through a filter by excitation light with a wavelength close to 590 nanometers, and a red fluorescent light signal with a wavelength close to 610 nanometers was observed through a filter. The test results are shown in FIGS. 30 to 32.

The red fluorescent light (white and gray areas in FIG. 30) and the green fluorescent light (white and gray areas in FIG. 31) were both observed in the same cells. Based on these results, it was confirmed that the method for manufacturing the exogenous substance-bearing cells in the sixth example, which was implemented using the apparatus 41, is able to introduce a plurality of genes into the target cells in a single operation. Thus, according to the method for manufacturing the exogenous substance-bearing cells that was implemented using the apparatus 41, a plurality of types of genes can be introduced into the target cells by a simple technique.

Seventh Example

The apparatus 61 that is shown in FIG. 10 was created by the procedure that is hereinafter described. An eight-lane reservoir (R08R01S, BM Equipment Co., Ltd.) was used as the processing container. Aluminum tapes (Furuto Industrial Co., Ltd.) with widths of 5 millimeters, which serve as the electrodes, were affixed to pairs of inner walls that face one another in the containers with which the processing container is provided. The gaps between the electrodes are 5 millimeters. Each one of the aluminum tapes was extended to the outside of the container at the top of the container and is affixed to the top plate of the processing container, which was formed between the columns of the containers. In the top plate, rectangular pieces of metal foil were disposed such that they flank the containers and extend along the direction of the rows of the containers. Each of the pieces of metal foil was in contact with the top faces (connecting portions) of the aluminum tapes that have been extended to the outside of the containers. One end of each of the pieces of metal foil was electrically connected to the positive electrode of the high-voltage power supply. The other end of each of the pieces of metal foil was electrically connected to the negative electrode of the high-voltage power supply. The voltage can thus be applied to each one of the containers.

A silicone oil with a kinematic viscosity of 100 cSt was poured into each of the eight containers and was left to stand. A pipette was used to supply 3 microliters of a xylene cyanol solution between the electrodes in the electrode portions of the individual containers, such that spherical liquid droplets with a diameter of approximately 1.8 millimeters were formed in the silicone oil. A voltage of 2.5 kV (electric field intensity of 3.6 kV/cm) was applied from the high-voltage direct current power supply. The confirmation of the movement of the liquid droplets was carried out by the same sort of technique as in the first example.

The states of movement of the liquid droplets are shown in FIGS. 33 to 36. As shown in FIGS. 33 to 36, it was confirmed that the liquid droplets (the black circular areas in FIGS. 33 to 36) moved back and forth between the electrodes in each of the plurality of the electrode portions. It was confirmed that the liquid droplets moved back and forth between the electrodes approximately 200 times in one minute. It was confirmed by the seventh example that the processing can be performed in parallel for a plurality of the liquid droplets within a single container. It is therefore suggested that the apparatus and the method in the seventh example are able to perform the processing that introduces the exogenous substance into the cells in parallel as many sets as there are electrodes, while maintaining safety.

Eighth Example

Rapeseed oil (Nacalai Tesque, Inc.) with a kinematic viscosity of 50 cSt was poured into a container in the same sort of apparatus as in the first example, up to a seventh demarcation, and was left to stand. A pipette was used to supply 3 microliters of a xylene cyanol solution to the container, such that a spherical liquid droplet with a diameter of approximately 1.8 millimeters was formed in the rapeseed oil. Next, a voltage of 2.8 kV (electric field intensity of 2.8 kV/cm) was applied by the high-voltage direct current power supply. The confirmation of the movements of the liquid droplet was carried out by the same sort of technique as in the first example.

The states of movement of the liquid droplet are shown in FIGS. 37 to 41. In FIGS. 37 to 41, the directions of movement of liquid droplet (the dark gray circular and elliptical areas in FIGS. 37 to 41) are indicated by arrows. The arrows in FIG. 39 indicate that after the liquid droplet had advanced to the right, it came into contact with the electrode on the right side in the figure, and its direction of movement was reversed. As shown in FIGS. 37 to 41, it was confirmed that the liquid droplet moves back and forth between the pair of the electrodes. It was confirmed that the liquid droplet moves back and forth between the aluminum tapes and comes into contact with the aluminum tapes approximately 150 times per minute. It is therefore suggested that the same sort of apparatus as in the first example, by using the method in the eighth example, is able to perform the processing that introduces the exogenous substance into the cells, even in a case where an insulating oil other than silicone oil is used as the insulating liquid.

Ninth Example

The apparatus 81 that is shown in FIG. 11 was created by the procedure that is hereinafter described. An eight-lane reservoir (R08R01S, BM Equipment Co., Ltd.), in which each of the containers (wells) has a width of 7 millimeters, was used as the container. Aluminum tapes (Furuto Industrial Co., Ltd.) with widths of 5 millimeters, which serve as the electrodes, are affixed to pairs of inner walls that face one another in the containers. The distance from the opening portion of the container to the bottom edges of the aluminum tapes is 5 millimeters. The end of the top face of one of the aluminum tapes that have been extended to the outside of each one of the containers was electrically connected to the positive electrode of the high-voltage power supply. The end of the top face of the other one of the aluminum tapes was electrically connected to the negative electrode of the high-voltage power supply. The voltage can thus be applied to each one of the containers. A fluorocarbon (Fluorinert FC-75, 3M Company) with a specific gravity that is greater than 1 and a silicone oil with a specific gravity from 0.9 to 1 and a kinematic viscosity of 30 cSt were poured into the containers and left to stand. Due to the difference in the specific gravities of fluorocarbon oil and the silicone oil, a layer of the silicone oil was formed on top of a layer of the fluorocarbon oil inside each one of the containers. Three microliters of ultrapure water that was manufactured using an ultrapure water manufacturing unit (Milli-Q, Millipore Corporation) was supplied by a pipette between the electrodes in each one of the containers, such that spherical liquid droplets with a diameter of approximately 1.8 millimeters were formed in the silicone oil. Next, a voltage of 2.5 kV (electric field intensity of 3.6 kV/cm) was applied from the high-voltage direct current power supply. The confirmation of the movements of the liquid droplets was carried out by the same sort of technique as in the first example.

It was confirmed that the liquid droplets move back and forth between the pair of the electrodes. It was confirmed that the liquid droplets move back and forth between the aluminum tapes and come into contact with the aluminum tapes approximately 200 times per minute. It is therefore suggested by the ninth example that the apparatus 81 is able to perform the processing that introduces the exogenous substance into the cells, even in a case where two types of insulating oil with different specific gravities are used as the insulating liquids.

Tenth Example

ICR mouse (16-day embryo) hippocampal nerve cells (Sumitomo Bakelite Co., Ltd.) were added to a Petri dish, into which had been poured a tissue dispersion liquid having papain enzyme as its main constituent, to a concentration of $1.5 \times 10^5$ cells per milliliter, and the cells were dispersed. The concentration of the hippocampal nerve cells was adjusted to a concentration of $1.5 \times 10^3$ cells per 2-microliter liquid droplet. The cell suspension liquid was prepared by adding two types of the plasmid DNA at the concentrations hereinafter described to the Petri dish. Specifically, the plasmid DNA 1, which encodes the yellow (yellow-green) fluorescent protein, was added at a concentration of 200 nanograms per microliter. The plasmid DNA 3, which encodes the red fluorescent protein, was added at a concentration of 150 nanograms per microliter. The apparatus 41 (refer to FIG. 8) that was created in the second example was used. The liquid droplets were formed by dripping the cell suspension liquid in 2-microliter droplets into the containers, which contained silicone oil with a kinematic viscosity of 30 cSt. A voltage of 2.1 kV was applied to the pairs of the electrodes for five minutes. After the voltage was applied, the liquid droplets that were recovered from the oil were added to a glass bottom plate (EZView Glass Bottom Culture Plate, Iwaki) with 24 wells, into which the prepared culture medium had been poured, and incubated under conditions of 37° C. and 5% carbon dioxide.

The cells were observed by microscope (Olympus IX81) seven days after the start of the culturing. With a mercury lamp light source serving as the light source, the target cells were illuminated through a filter by excitation light with a wavelength close to 490 nanometers and were observed by passing a green fluorescent signal with a wavelength close to 510 nanometers through a filter. With a mercury lamp light source serving as the light source, the target cells were illuminated through a filter by excitation light with a wavelength close to 590 nanometers and were observed by passing a red fluorescent signal with a wavelength close to 610 nanometers through a filter (observation magnification 60×).

Seven days after the start of the culturing, the red fluorescent light and the green fluorescent light were both observed in the same cells, although this has been omitted from the figures. Based on these results, it was confirmed that the method for manufacturing the exogenous substance-bearing cells in the tenth example, which was implemented using the apparatus 41, is able to introduce a plurality of genes into the target cells, even into first-generation mouse hippocampal cells, in a single operation. Thus, according to the method for manufacturing the exogenous substance-bearing cells that was implemented using the apparatus 41, a plurality of types of genes can be introduced into the target cells by a simple technique.

DESCRIPTION OF THE REFERENCE NUMERALS 1, 11, 41, 61, 81 exogenous substance transfer apparatus
6, 46 oil
2, 12, 62, 82 container
5a, 5b, 15a, 15b, 25a, 25b, 35a, 35b electrode
5, 15, 25, 35 electrode portion
9 power supply
15a1, 15b1, 35a1 sheet portion
45, 65 plate-shaped strip portion
45a, 45b, 65a, 65b plate-shaped strip

The invention claimed is:
1. An exogenous substance transfer apparatus configured to introduce an exogenous substance into a cell from outside the cell by electrical action, comprising:
   at least one storage vessel having an opening through which a substance can be supplied from the outside;
   at least one electrode portion including a pair of electrodes, the at least one electrode portion disposed inside the at least one storage vessel, the pair of electrodes being separated from one another extending in a direction that is intersectional to a horizontal plane, each of the pair of the electrodes having an inside portion being disposed inside the at least one storage vessel, the inside portion of each of said pair of electrodes comprising a minimum length extending in a direction that is orthogonal to the horizontal plane being greater than a maximum length of the inside portion extending in a direction that is orthogonal to an opposite side wall of the storage vessel, and the minimum length of the inside portion extending in a direction that is orthogonal to the horizontal plane being greater than a diameter of a liquid droplet of a cell suspension liquid;

an electric field generating portion configured to generate an electric field by applying a direct current voltage to the at least one electrode portion for a specified length of time, and the electric field generating portion being configured, when applying the direct current voltage to the at least one electrode portion, to cause the liquid droplet to move toward an opposite polarity electrode and to cause the liquid droplet to reverse its direction of movement by causing the liquid droplet to come into contact with the opposite polarity electrode, the opposite polarity electrode being one of the pair of the electrodes whose polarity is an opposite of a polarity of the liquid droplet, the direct current voltage being applied in a state in which the cell suspension liquid has been supplied between the pair of the electrodes in each of the at least one storage vessel storing an insulating liquid to form the liquid droplet in the insulating liquid, the cell suspension liquid containing an exogenous substance and a cell, the cell suspension liquid not being capable of being mixed with the insulating liquid, and the diameter of the liquid droplet being smaller than a gap between the pair of the electrodes.

2. The exogenous substance transfer apparatus according to claim 1, wherein:
the at least one storage vessel has a bottom face portion;
the pair of the electrodes are separated from the bottom face portion in the direction that is orthogonal to the horizontal plane;
the minimum length of the inside portion extending in a direction that is orthogonal to the horizontal plane being substantially equal to a height of the opposite side wall of the storage vessel, the height of the opposite side wall extending in a direction that is orthogonal to the horizontal plane; and
the liquid droplet is separated from the bottom face of the storage vessel in the state in which the cell suspension liquid has been supplied between the pair of the electrodes.

3. The exogenous substance transfer apparatus according to claim 2, wherein:
the one of the pair of the electrodes includes a first sheet portion, the first sheet portion being a sheet portion that extends in a direction that is substantially orthogonal to the horizontal plane, the first sheet portion being a sheet portion formed to be curved into a substantially circular arc in which a side that faces the other electrode is dented.

4. The exogenous substance transfer apparatus according to claim 3, wherein:
the other of the pair of the electrodes includes a second sheet portion, the second sheet portion being a sheet portion that extends in a direction that is substantially orthogonal to the horizontal plane, the second sheet portion being a sheet portion formed to be curved into a substantially circular arc in which a side that faces the one of the electrodes is dented.

5. The exogenous substance transfer apparatus according to claim 1, wherein:
at least one of the pair of the electrodes includes one of concave portion and convex portion.

6. The exogenous substance transfer apparatus according to claim 1, wherein:
the gap between the pair of the electrodes is not greater than one centimeter, and
the electric field generating portion is configured to move the liquid droplet that is formed between the pair of the electrodes back and forth between the pair of the electrodes a plurality of times by repeating a cycle in which the electric field generating portion causes the liquid droplet to move toward the opposite polarity electrode and causes the liquid droplet to reverse its direction of movement by causing the liquid droplet to come into contact with the opposite polarity electrode.

7. The exogenous substance transfer apparatus according to claim 1, wherein the pair of electrodes extends to at least the opening portion.

8. The exogenous substance transfer apparatus according to claim 1, wherein:
the at least one storage vessel is a plurality of the storage vessels arrayed in parallel, the opening portion being formed in a top face of each one of the plurality of the storage vessels, one of the electrode portion being provided in each one of the plurality of the storage vessels,
each one of the pair of the electrodes extends to at least the opening portion,
the exogenous substance transfer apparatus further comprises:
a first connecting portion that electrically connects to one of the pair of the electrodes in the opening portion of each one of the plurality of the storage vessels; and
a second connecting portion that electrically connects to the other of the pair of the electrodes in the opening portion of each one of the plurality of the storage vessels, and
the electric field generating portion applies the direct current voltage to the one electrode portion in each one of the plurality of the storage vessels through the first connecting portion and the second connecting portion.

9. The exogenous substance transfer apparatus according to claim 1, wherein:
each one of the at least one storage vessel contains a plurality of the electrode portions, which are disposed with gaps between each of the plurality of the electrode portions,
each one of the pair of the electrodes extends to at least the opening portion,
the exogenous substance transfer apparatus further comprises:
a first connecting portion that electrically connects to one of the pair of the electrodes in the opening portion of each one of the at least one storage vessel; and
a second connecting portion that electrically connects to the other of the pair of the electrodes in the opening portion of each one of the at least one storage vessel, and
the electric field generating portion applies the direct current voltage to the plurality of the electrode portion in each one of the at least one storage vessel through the first connecting portion and the second connecting portion.

10. A method for manufacturing an exogenous substance-bearing cell using the exogenous substance transfer apparatus according to claim 1, the method comprising:

a first process that, by supplying the cell suspension liquid that contains the cell and at least one type of the exogenous substance to the insulating liquid, forms the liquid droplet in the insulating liquid, the insulating liquid being stored in the storage vessel, and the insulating liquid being not capable of being mixed with mix with the cell suspension liquid; and a second process that introduces the at least one type of into the cell in the liquid droplet by applying the direct current voltage for a specified length of time to the pair of electrodes that are provided on both sides of the liquid droplet that was formed in the first process, the pair of the electrodes extending in the direction that is intersectional to the surface of the insulating liquid, the applying of the direct current voltage causing the liquid droplet to move back and forth between one and the other of the pair of the electrodes and to come into contact with the pair of the electrodes.

11. The method for manufacturing the exogenous substance-bearing cell according to claim 10, wherein the second process is a process that introduces the at least one type of exogenous substance into a nucleus of the cell.

12. The method for manufacturing the exogenous substance-bearing cell according to claim 10, wherein the first process is a process that forms the liquid droplet by supplying to the insulating liquid a cell suspension liquid that contains a plurality of types of exogenous substances, and the second process is a process that introduces the plurality of types of the exogenous substances into the cell by applying the direct current voltage for the specified length of time.

13. The method for manufacturing the exogenous substance-bearing cell according to claim 10, wherein the cell that is used in the first process is at least one of a human somatic cell and a somatic cell from an animal other than a human.

14. The method for manufacturing the exogenous substance-bearing cell according to claim 10, wherein the insulating liquid includes a first insulating liquid and a second insulating liquid whose specific gravity is less than that of the first insulating liquid, the method for manufacturing the exogenous substance-bearing cell further comprises:

a pouring process that, prior to the first process, pours the first insulating liquid and the second insulating liquid into the storage vessel, causing a layer of the second insulating liquid to form above a layer of the first insulating liquid, the first process is a process that forms the liquid droplet within the second insulating liquid, and the second process is a process that moves the liquid droplet back and forth within the second insulating liquid by applying the direct current voltage to the pair of the electrodes for the specified length of time.

* * * * *